US006921649B2

(12) United States Patent
Piddington et al.

(10) Patent No.: US 6,921,649 B2
(45) Date of Patent: Jul. 26, 2005

(54) POLYNUCLEOTIDE ENCODING ADIPOCYTE COMPLEMENT RELATED PROTEIN HOMOLOG ZACRP2

(75) Inventors: Christopher S. Piddington, Thousand Oaks, CA (US); Paul D. Bishop, Fall City, WA (US)

(73) Assignee: ZymoGenetics, Inc., Seattle, WA (US)

( * ) Notice: Subject to any disclaimer, the term of this patent is extended or adjusted under 35 U.S.C. 154(b) by 12 days.

(21) Appl. No.: 10/621,787

(22) Filed: Jul. 17, 2003

(65) Prior Publication Data

US 2004/0024187 A1 Feb. 5, 2004

Related U.S. Application Data

(62) Division of application No. 09/552,204, filed on Apr. 19, 2000, now Pat. No. 6,620,909.
(60) Provisional application No. 60/130,207, filed on Apr. 20, 1999.

(51) Int. Cl.$^7$ .......................... C12P 21/02; C12N 1/00; C12N 5/10; C12N 15/12; C12N 15/62; C12N 15/63
(52) U.S. Cl. ................... 435/69.1; 435/243; 435/320.1; 435/325; 435/419; 536/23.1; 536/23.4; 536/23.5
(58) Field of Search .............................. 536/23.1, 23.5, 536/23.4; 435/320.1, 325, 419, 243, 69.1

(56) References Cited

U.S. PATENT DOCUMENTS 6,150,502 A   11/2000   Strachan

FOREIGN PATENT DOCUMENTS

| WO | 96/39429 | 12/1996 |
| WO | 99/55865 | 11/1999 |
| WO | 99/59618 | 11/1999 |
| WO | 99/64629 | 12/1999 |
| WO | 00/64943 | 11/2000 |

OTHER PUBLICATIONS

Scherer et al., *J. Biol. Chem.* 270: 26746–26749, 1995.
Nakano et al., *J. Biochem.* 120: 803–812, 1996.
Maeda et al., *Biochem, Biophys. Res. Comm.* 221: 286–289, 1996.
Marra et al., WashU–HHMI Mouse EST Project, 1996, GenBank Accession No. W41045.
Hillier et al., WashU–Merck EST Project, 1996, GenBank Accession No. W79559.
Hillier et al., WashU–Merck EST Project, 1996, GenBank Accession No. W79527.
Hillier et al., WashU–Merck EST Project, 1996, GenBank Accession No. W93527.
Incyte Pharmaceuticals Inc, INC2207141, 1996.
Incyte Pharmaceuticals Inc., INC2211943, 1996.
Incyte Pharmaceuticals Inc. SINTFET03, 1996.
TIGR Tentative Human Consensus Sequence, THC–THC164043, 1996.
Shapiro et al., *Current Biol.*. 8: 335–338, 1998.
Wilson, WashUMerck EST Project, 1997, GenBank Accession No. AA194106.
Kerlavage, The Institute for Genomic Research, GenBank Accession No. AA346195, 1997.
Hillier et al., WashU–Merck EST Project, GenBank Accession No. AA43244, 1997.
Hillier et al., WashU–Merck EST Project, GenBank Accession No. AA443206, 1997.
Incyte Pharmaceuticals, Inc., INC2240790, 1997.
Incyte Pharmaceuticals, Inc. INC2532555, 1997.
Incyte Pharmaceuticals, Inc. INC3330364, 1997.
Incyte Pharmaceuticals, Inc. INC3452732, 1997.
Incyte Pharmaceuticals, Inc. INC2412827, 1997.
Incyte Pharmaceuticals, Inc. INC3219860, 1997.
Incyte Pharmaceuticals, Inc. INC3564688, 1997.
Incyte Pharmaceuticals, Inc. INC 3221716, 1997.
Incyte Pharmaceuticals, Inc. INC3722062, 1997.
Incyte Pharmaceuticals, Inc., Library GBLANOT02, 1997.
Incyte Pharmaceuticals, Inc., Library PANCTUT02, 1997.
Incyte Pharmaceuticals, Inc., Library HEAONOT04, 1997.
Incyte Pharmaceuticals, Inc., Library UTRSNON03, 1997.
Incyte Pharmaceuticals, Inc., Library BSTMNON02, 1997.
Incyte Pharmaceuticals, Inc., Library COLNNON03, 1997.
Incyte Pharmaceuticals, Inc., Library SKINNOT05, 1997.
Incyte Pharmaceuticals, Inc., Library PENCNOT10, 1997.
Myers, Stanford Human Genome Center, 1998, Accession No. G37397.
Hillier et al., WashU–NCI Human EST Project, GenBank Accession No. AA732948, 1998.
Marra M/Mouse EST Project, GenBank Accession No. AI324802, 1998.
Strausberg, NCI, Cancer Genome Anatomy Project, GenBank Accession No. AI288625, 1998.
Strausberg, NCI, Cancer Genome Anatomy Project, GenBank Accession No. AI038644, 1998.
Incyte Pharmaceuticals, Inc., INC4052530, 1998.
Incyte Pharmaceuticals, Inc., INC5154455, 1998.
Incyte Pharmaceuticals, Inc., INC5155056, 1998.
Incyte Pharmaceuticals, Inc., Library HEARFET03, 1998.
Incyte Pharmaceuticals, Inc., Library SINTNOT18, 1998.
Ouchi et al., *Circulation 100:* 2473–2476, 1999.
Incyte Pharmaceuticals, Inc., INC5440206, 1999.
Incyte Pharmaceuticals, Inc. INCLUNGNOT40, 1999.

*Primary Examiner*—Terry McKelvey
(74) *Attorney, Agent, or Firm*—Brian J. Walsh

(57) ABSTRACT

The present invention relates to polynucleotide and polypeptide molecules for zacrp2, a novel member of the family of proteins bearing a collagen-like domain and a C1q domain. The polypeptides and polynucleotides encoding them, are involved in dimerization or oligomerization and may be used in the study thereof. The present invention also includes antibodies to the zacrp2 polypeptides.

27 Claims, 1 Drawing Sheet

```
            10         20         30         40         50
C1QC_HUMAN  MDVGPSSLPHLGLKLLLLLLLLALRGQANT------------------- 30
ACR3_HUMAN  MLLLGAVLLLLALPGHDQETTTQGPGVLLPLPKGACTGWMA--------- 41
HUZACRP2    MIPWVLLACALPCAADPLLGAFARRDFRKGSPQLVCSLP----------- 39

60         70         80         90         100
C1QC_HUMAN  ---------GCYGIPGMPGLPGAPGKDGYDGLPGPKGEPGIPAIPGIRGP 71
ACR3_HUMAN  GIPGHPGHNGAPGRDGRDGTPGEKGEKGDPGLIGPKGDIGETGVPGAEGP 91
HUZACRP2    GPQGPPGPPGAPGPSGMMGRMGFPGKDGQDGHDGDRGDSGEEGPPGRTGN 89

110        120        130        140        150
C1QC_HUMAN  KGQKGEPGLPGHPGKNGPMGPPGMPGVPGPMGIPGEPGEEGRY------- 114
ACR3_HUMAN  RGFPGIQGRKGEP------------------------------------- 104
HUZACRP2    RGKPGPKGKAGAIGRAGPRGPKGVNGTPGKHGTPGKKGPKGKKGEPGLPG 139

160        170        180        190        200
C1QC_HUMAN  ----KQKFQSVFTVTRQTHQPPAPNSLIRFNAVLTNPQGDYDTSTGKFTC 160
ACR3_HUMAN  --GEGAYVYRSAFSVGLETYVTIPNMPIRFTKIFYNQQNHYDGSTGKFHC 152
HUZACRP2    PCSCGSGHTKSAFSVAVTKSYPRERLPIKFDKILMNEGGHYNASSGKFVC 189

210        220        230        240        250
C1QC_HUMAN  KVPGLYYFVYHAS-HTANLCVLLYRSG---VKVVTFCGHTSKTNQVN--S 204
ACR3_HUMAN  NIPGLYYFAYHITVYMKDVKVSLFKK----DKAMLFTYDQYQENNVDQAS 198
HUZACRP2    GVPGIYYFTYDITLANKHLAIGLV--HNGQYRIRTFDANTG-NHDVA--S 234

260        270        280        290        300
C1QC_HUMAN  GGVLLRLQVGEEVWLAVNDYYDMVGIQG----SDSVFSGFLLFPD----- 245
ACR3_HUMAN  GSVLLHLEVGDQVWLQVYGEGERNGLYAD-NDNDSTFTGFLLYHDTN--- 244
HUZACRP2    GSTILALKQGDEVWLQIF-YSEQNGLFYDPYWTDSLFTGFLIYADQDDPN 283

C1QC_HUMAN  --
ACR3_HUMAN  --
HUZACRP2    EV  285
```

Figure

POLYNUCLEOTIDE ENCODING ADIPOCYTE COMPLEMENT RELATED PROTEIN HOMOLOG ZACRP2

REFERENCE TO RELATED APPLICATIONS

The present application is a divisional of U.S. patent application Ser. No. 09/552,204, filed Apr. 19, 2000, now U.S. Pat. No. 6,620,909 B1, which claims the benefit of U.S. Patent Application Ser. No. 60/130,207, filed Apr. 20, 1999, both of which are herein incorporated by reference.

BACKGROUND OF THE INVENTION

Energy balance (involving energy metabolism, nutritional state, lipid storage and the like) is an important criteria for health. This energy homeostasis involves food intake and metabolism of carbohydrates and lipids to generate energy necessary for voluntary and involuntary functions. Metabolism of proteins can lead to energy generation, but preferably leads to muscle formation or repair. Among other consequences, a lack of energy homeostasis lead to over or under formation of adipose tissue.

Formation and storage of fat is insulin-modulated. For example, insulin stimulates the transport of glucose into cells, where it is metabolized into α-glycerophosphate which is used in the esterification of fatty acids to permit storage thereof as triglycerides. In addition, adipocytes (fat cells) express a specific transport protein that enhances the transfer of free fatty acids into adipocytes.

Adipocytes also secrete several proteins believed to modulate homeostatic control of glucose and lipid metabolism. These additional adipocyte-secreted proteins include adipsin, complement factors C3 and B, tumor necrosis factor α, the ob gene product and Acrp30. Evidence also exists suggesting the existence of an insulin-regulated secretory pathway in adipocytes. Scherer et al., *J. Biol. Chem.* 270 (45): 26746–9, 1995. Over or under secretion of these moieties, impacted in part by over or under formation of adipose tissue, can lead to pathological conditions associated directly or indirectly with obesity or anorexia.

Acrp30 is a 247 amino acid polypeptide that is expressed exclusively by adipocytes. The Acrp30 polypeptide is composed of a amino-terminal signal sequence, a 27 amino acid stretch of no known homology, 22 perfect Gly-Xaa-Pro or imperfect Gly-Xaa-Xaa collagen repeats and a carboxy terminal globular domain. See, Scherer et al. as described above and International Patent Application No. WO 96/39429. Acrp30, an abundant human serum protein regulated by insulin, shares structural similarity, particularly in the carboxy-terminal globular domain, to complement factor C1q and to a summer serum protein of hibernating Siberian chipmunks (Hib27). Expression of Acrp30 is induced over 100-fold during adipocyte differentiation. Acrp30 is suggested for use in modulating energy balance and in identifying adipocytes in test samples.

Another secreted protein that appears to be exclusively produced in adipocytes is apM1, described, for example, in Maeda et al., *Biochem. Biophys. Res. Comm.* 221: 286–9, 1996. A 4517 bp clone had a 244 amino acid open reading frame and a long 3' untranslated region. The protein included a signal sequence, an amino-terminal non-collagenous sequence, 22 collagen repeats (Gly-XAA-Pro or Gly-Xaa-Xaa), and a carboxy-terminal region with homology to collagen X, collagen VIII and complement protein C1q.

Complement factor C1q consists of six copies of three related polypeptides (A, B and C chains), with each polypeptide being about 225 amino acids long with a near amino-terminal collagen domain and a carboxy-terminal globular region. Six triple helical regions are formed by the collagen domains of the six A, six B and six C chains, forming a central region and six stalks. A globular head portion is formed by association of the globular carboxy terminal domain of an A, a B and a C chain. C1q is therefore composed of six globular heads linked via six collagen-like stalks to a central fibril region. Sellar et al., *Biochem. J.* 274: 481–90, 1991. This configuration is often referred to as a bouquet of flowers. Acrp30 has a similar bouquet structure formed from a single type of polypeptide chain.

C1q has been found to stimulate defense mechanisms as well as trigger the generation of toxic oxygen species that can cause tissue damage (Tenner, *Behring Inst. Mitt.* 93:241–53, 1993). C1q binding sites are found on platelets. Additionally complement and C1q play a role in inflammation. The complement activation is initiated by binding of C1q to immunoglobulins Inhibitors of C1q and the complement pathway would be useful for anti-inflammatory applications, inhibition of complement activation and thrombotic activity.

The present invention provides such polypeptides for these and other uses that should be apparent to those skilled in the art from the teachings herein.

SUMMARY OF THE INVENTION

Within one aspect the invention provides an isolated polypeptide comprising a sequence of amino acid residues that is at least 75% identical in amino acid sequence to residues 40–285 of SEQ ID NO:2, wherein the sequence comprises: Gly-Xaa-Xaa or Gly-Xaa-Pro repeats forming a collagen domain, wherein Xaa is any amino acid; and a carboxyl-terminal C1q domain comprises 10 beta strands. Within one embodiment the polypeptide that is at least 90% identical in amino acid sequence to residues 16–285 of SEQ ID NO:2. Within another embodiment the collagen domain consists of 24 Gly-Xaa-Xaa repeats and 10 Gly-Xaa-Pro repeats. Within another embodiment the carboxyl-terminal C1q domain comprises the sequence of SEQ ID NO:5. Within another embodiment the carboxy-terminal C1q domain comprises amino acid residues 151–155, 172–174, 180–183, 187–190, 193–205, 208–214, 220–227, 229–241, 246–251 and 269–274 of SEQ ID NO:2. Within another embodiment any differences between said polypeptide and SEQ ID NO:2 are due to conservative amino acid substitutions. Within another embodiment the polypeptide specifically binds with an antibody that specifically binds with a polypeptide consisting of the amino acid sequence of SEQ ID NO:2. Within a further embodiment the polypeptide comprises residues 16–285 of SEQ ID NO:2. Within another embodiment the polypeptide is covalently linked at the amino or carboxyl terminus to a moiety selected from the group consisting of affinity tags, toxins, radionucleotides, enzymes and fluorophores. Within yet another embodiment the collagen domain consists of amino acid residues 41–141 of SEQ ID NO:2. Within another embodiment the carboxy-terminal C1q domain consists of amino acid residues 142–285 of SEQ ID NO:2.

The invention also provides an isolated polypeptide selected from the group consisting of: a) a polypeptide consisting of a sequence of amino acid residues that is 75% identical in amino acid sequence to amino acid residue 40 to amino acid residue 141 of SEQ ID NO:2; b) a polypeptide consisting of a sequence of amino acid residues that is 75% identical in amino acid sequence to amino acid residue 142 to amino acid residue 285 of SEQ ID NO:2; and c) a polypeptide consisting of a sequence of amino acid residues that is 75% identical in amino acid sequence to amino acid residue 40 to 285 of SEQ ID NO:2.

Within another aspect, the invention provides a fusion protein comprising a first portion and a second portion joined by a peptide bond, the first portion consisting of a polypeptide selected from the group consisting of: a) a polypeptide comprising a sequence of amino acid residues that is at least 75% identical in amino acid sequence to amino acid residue 16 to amino acid residue 285 of SEQ ID NO:2; b) a polypeptide comprising a sequence of amino acid residues as shown in SEQ ID NO:2 from amino acid residue 1 to amino acid residue 281; c) a polypeptide comprising a sequence of amino acid residues as shown in SEQ ID NO:2 from amino acid residue 16 to amino acid residue 285; d) a portion of the zacrp2 polypeptide as shown in SEQ ID NO:2, comprising the collagen-like domain or a portion of the collagen-like domain capable of dimerization or oligomerization; e) a portion of the zacrp2 polypeptide as shown in SEQ ID NO:2, comprising the C1q domain or an active portion of the C1q domain; or f) a portion of the zacrp2 polypeptide as shown in SEQ ID NO:2 comprising of the collagen-like domain and the C1q domain; and the second portion comprising another polypeptide. Within one embodiment the first portion is selected from the group consisting of: a) a polypeptide consisting of the sequence of amino acid residue 40 to amino acid residue 141 of SEQ ID NO:2; b) a polypeptide consisting of the sequence of amino acid residue 142 to amino acid residue 285 of SEQ ID NO:2; c) a polypeptide consisting of the sequence of amino acid residue 40 to 285 of SEQ ID NO:2.

Within another aspect, the invention provides a polypeptide as described above; in combination with a pharmaceutically acceptable vehicle.

Within another aspect is provided an antibody or antibody fragment that specifically binds to a polypeptide as described above. Within one embodiment the antibody is selected from the group consisting of: a) polyclonal antibody; b) murine monoclonal antibody; c) humanized antibody derived from b); and d) human monoclonal antibody. Within another embodiment the antibody fragment is selected from the group consisting of F(ab'), F(ab), Fab', Fab, Fv, scFv, and minimal recognition unit. Within another embodiment is provided an anti-idiotype antibody that specifically binds to the antibody described above.

Within another aspect, the invention provides an isolated polynucleotide selected from the group consisting of: a) a polynucleotide encoding a polypeptide comprising a sequence of amino acid residues that is at least 75% identical in amino acid sequence to residues 40–285 of SEQ ID NO:2, wherein the sequence comprises: Gly-Xaa-Xaa or Gly-Xaa-Pro repeats forming a collagen domain, wherein Xaa is any amino acid; and a carboxyl-terminal C1q domain comprising 10 beta strands. Within one embodiment the polypeptide is at least 90% identical in amino acid sequence to residues 16–285 of SEQ ID NO:2. Within another embodiment the collagen domain consists of 24 Gly-Xaa-Xaa repeats and 10 Gly-Xaa-Pro repeats. Within yet another embodiment the carboxyl-terminal C1q domain comprises the sequence of SEQ ID NO:5. Within another embodiment the carboxy-terminal C1q domain comprises amino acid residues 151–155, 172–174, 180–183, 187–190, 193–205, 208–214, 220–227, 229–241, 246–251 and 269–274 of SEQ ID NO:2. Within another embodiment any differences between said polypeptide and SEQ ID NO:2 are due to conservative amino acid substitutions. Within another embodiment the polynucleotide encodes a polypeptide that specifically binds with an antibody that specifically binds with a polypeptide consisting of the amino acid sequence of SEQ ID NO:2. Within still another embodiment the polynucleotide encodes a polypeptide that comprises residues 16–285 of SEQ ID NO:2. Within another embodiment the collagen domain consists of amino acid residues 41–141 of SEQ ID NO:2. Within yet another embodiment the carboxy-terminal C1q domain consists of amino acid residues 142–285 of SEQ ID NO:2.

Also provided is an isolated polynucleotide selected from the group consisting of: a) a sequence of nucleotides from nucleotide 1 to nucleotide 1161 of SEQ ID NO:1; b) a sequence of nucleotides from nucleotide 133 to nucleotide 987 of SEQ ID NO:1; c) a sequence of nucleotides from nucleotide 178 to nucleotide 987 of SEQ ID NO:1; d) a sequence of nucleotides from nucleotide 250 to nucleotide 987 of SEQ ID NO:1; e) a sequence of nucleotides from nucleotide 556 to nucleotide 987 of SEQ ID NO:1; f) a sequence of nucleotides from nucleotide 133 to nucleotide 555 of SEQ ID NO:1; g) a sequence of nucleotides from nucleotide 178 to nucleotide 555 of SEQ ID NO:1; h) a sequence of nucleotides from nucleotide 250 to nucleotide 555 of SEQ ID NO:1; i) a polynucleotide encoding a polypeptide, the polypeptide consisting of a sequence of amino acid residues that is at least 75% identical to a polypeptide consisting of the amino acid sequence of residues 40 to 141 of SEQ ID NO:2; j) a polynucleotide encoding a polypeptide, the polypeptide consisting of a sequence of amino acid residues that is at least 75% identical to a polypeptide consisting of the amino acid sequence of residues 142 to 285 of SEQ ID NO:2; k) a polynucleotide encoding a polypeptide, the polypeptide consisting of a sequence of amino acid residues that is at least 75% identical to a polypeptide consisting of the amino acid sequence of residues 40 to 285 of SEQ ID NO:2; l) a polynucleotide encoding a polypeptide consisting of a sequence of amino acid residues that is at least 75% identical to a polypeptide consisting of the amino acid sequence of residues 16 to 141 of SEQ ID NO:2; m) a polynucleotide that remains hybridized following stringent wash conditions to a polynucleotide consisting of the nucleotide sequence of SEQ ID NO:1, or the complement of SEQ ID NO:1; n) nucleotide sequences complementary to a), b), c), d), e), f), g), h), i), j), k), l) or m) and o) degenerate nucleotide sequences of i), j), k) or l).

The invention further provides an isolated polynucleotide encoding a fusion protein comprises a first portion and a second portion joined by a peptide bond, the first portion is selected from the group consisting of: a) a polypeptide comprising a sequence of amino acid residues that is at least 75% identical in amino acid sequence to amino acid residues 40 to 285 of SEQ ID NO:2; b) a polypeptide comprising the sequence of amino acid residues 1 to 285 of SEQ ID NO:2; c) a polypeptide comprising the sequence of amino acid residues 16 to 285 of SEQ ID NO:2; d) a portion of a polypeptide of SEQ ID NO:2 comprising the collagen-like domain or a portion of the collagen-like domain capable of dimerization or oligomerization; e) a portion of the polypeptide of SEQ ID NO:2 containing the C1q domain; or f) a portion of the polypeptide of SEQ ID NO:2 including the collagen-like domain and the C1q domain; and the second portion comprising another polypeptide.

Also provided is an isolated polynucleotide consisting of the sequence of nucleotide 1 to nucleotide 855 of SEQ ID NO:10.

Within another aspect, the invention provides an expression vector comprising the following operably linked elements: a transcription promoter; a DNA segment encoding a polypeptide as described above; and a transcription terminator. Within one embodiment the DNA segment encodes a polypeptide that is at least 90% identical in amino acid sequence to residues 16–285 of SEQ ID NO:2. Within another embodiment the collagen domain consists of 24 Gly-Xaa-Xaa repeats and 10 Gly-Xaa-Pro repeats. Within another embodiment the carboxyl-terminal C1q domain comprises the sequence of SEQ ID NO:5. Within another embodiment the carboxy-terminal C1q domain comprises amino acid residues 151–155, 172–174, 180–183, 187–190, 193–205, 208–214, 220–227, 229–241, 246–251 and 269–274 of SEQ ID NO:2. Within another embodiment any differences between said polypeptide and SEQ ID NO:2 are due to conservative amino acid substitutions. Within another embodiment the collagen domain consists of amino acid residues 41–141 of SEQ ID NO:2. Within another embodiment the carboxy-terminal C1q domain consists of amino acid residues 142–285 of SEQ ID NO:2. Within yet another embodiment the polypeptide specifically binds with an antibody that specifically binds with a polypeptide consisting of the amino acid sequence of SEQ ID NO:2. Within yet another embodiment the DNA segment encodes a polypeptide comprising residues 16–285 of SEQ ID NO:2. Within a further embodiment the DNA segment encodes a polypeptide covalently linked at the amino or carboxyl terminus to an affinity tag. Within another embodiment the DNA segment further encodes a secretory signal sequence operably linked to the polypeptide. Within a related embodiment the secretory signal sequence comprises residues 1–15 of SEQ ID NO:2.

Within another aspect, the invention provides a cultured cell into which has been introduced an expression vector as described above, wherein the cell expresses the polypeptide encoded by the DNA segment.

Within still another aspect, the invention a method of producing a polypeptide comprising: culturing a cell into which has been introduced an expression vector as described above; whereby the cell expresses the polypeptide encoded by the DNA segment; and recovering the expressed polypeptide.

BRIEF DESCRIPTION OF THE DRAWINGS

The FIGURE illustrates a multiple alignment of and zacrp2 polypeptide of the present invention and human ACRP30 (ACR3) (SEQ ID NO:3, Maeda et al., *Biochem. Biophys. Res. Commun.* 221:286–9, 1996) and human C1q C (SEQ ID NO:4, Sellar et al., *Biochem J.* 274:481–90, 1991 and Reid, *Biochem J.* 179:361–71, 1979). The multiple alignment performed using a Clustalx multiple alignment tool with the default settings: Blosum Series Weight Matricies, Gap Opening penalty:10.0, Gap Extension penalty:0.05. Multiple alignments were further hand tuned before computing percent identity.

DETAILED DESCRIPTION OF THE INVENTION

Prior to setting forth the invention in detail, it may be helpful to the understanding thereof to define the following terms.

The term "affinity tag" is used herein to denote a peptide segment that can be attached to a polypeptide to provide for purification or detection of the polypeptide or provide sites for attachment of the polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), substance P, Flag™ peptide (Hopp et al., *Biotechnology* 6:1204–10, 1988; available from Eastman Kodak Co., New Haven, Conn.), streptavidin binding peptide, or other antigenic epitope or binding domain. See, in general Ford et al., *Protein Expression and Purification* 2: 95–107, 1991. DNAs encoding affinity tags are available from commercial suppliers (e.g., Pharmacia Biotech, Piscataway, N.J.).

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a protein is located proximal to the carboxyl terminus of the reference sequence, but is not necessarily at the carboxyl terminus of the complete protein.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' (SEQ ID NO:21) are 5'-TAGCTTgagtct-3' (SEQ ID NO:22) and 3'-gtcgacTACCGA-5' (SEQ ID NO:23).

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, denotes that the segments are arranged so that they function in concert for their intended purposes, e.g. transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

The term "promoter" denotes a portion of a gene containing DNA sequences that provide for the binding of RNA polymerase and initiation of transcription. Promoter sequences are commonly, but not always, found in the 5' non-coding regions of genes.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a polypeptide having homology to an adipocyte complement related protein (Acrp30). The novel DNA sequence encodes a polypeptide having an amino-terminal signal sequence, an adjacent N-terminal region of non-homology, a collagen domain composed of 34 Gly-Xaa-Xaa or Gly-Xaa-Pro repeats and a carboxy-terminal globular-like C1q domain. The general polypeptide structure set forth above is shared by Acrp30 and C1q C, except that the collagen-like domain of zacrp2 is longer than that of the other polypeptides. Moreover, the sequences aligned in the FIGURE share a conserved cysteine residue at position 189 of the zacrp2 polypeptide (SEQ ID NO:2). Other regions of homology, found in the carboxy-terminal globular C1q domain in the aligned proteins, are identified herein as useful primers for searching for other family members. Acrp30 and C1q C, for example, would be identified in a search using the primers. Also, the zacrp2 polypeptides of the present invention include a putative N-linked glycosylation site at amino acid 181 (Asn) of SEQ ID NO:2 and intra-chain disulfide bonding may involve the cysteine at residue 36 of SEQ ID NO:2.

Analysis of the tissue distribution of the mRNA corresponding to this novel DNA using a full length probe showed that zacrp2 is strongly represented in heart, small intestine and colon. Zacrp2 is also expressed in prostate, testis, liver, stomach, thyroid, spinal cord, uterus and trachea. The polypeptide has been designated zacrp2 polypeptide.

The novel zacrp2 polypeptides of the present invention were initially identified by querying an EST database for homologs of ACRP30 sequences, characterized by a signal sequence, a collagen-like domain and a C1q domain. Polypeptides corresponding to ESTs meeting those search criteria were compared to known sequences to identify proteins having homology to ACRP30. An assembled EST cluster was discovered and predicted to be a secreted protein. To identify the corresponding cDNA, a clone considered likely to contain the entire coding sequence was used for sequencing. The resulting 1161 bp sequence is disclosed in SEQ ID NO:1. Comparison of the originally derived EST sequences with the sequence represented in SEQ ID NO:1 showed that there were two frame shifts and a 203 bp insertion through the collagen-like domain. The novel polypeptide encoded by the full length cDNA enabled the identification of a homolog relationship with adipocyte complement related protein Acrp30 (SEQ ID NO:3) and complement component C1q C (SEQ ID NO:4) as is shown in the FIGURE. Zacrp2 shares 35.5 and 36.5% identity at the amino acid level with human C1q C and ACRP30 respectfully. C1q C and ACRP30 share 32% identity. Within the C1q domain, zacrp2 shares 33.6 and 40% identity at the amino acid level when compared to human C1q C and ACRP30 respectfully. C1q C and ACRP30 share 38.2% identity over this region.

The full sequence of the zacrp2 polypeptide was obtained from a single clone believed to contain it, wherein the clone was obtained from a pancreatic tumor tissue library. Other libraries that might also be searched for such clones include heart, small intestine, colon, prostate, testis, liver, stomach, thyroid, spinal cord, uterus trachea, adipose tissue and the like.

The nucleotide sequence of zacrp2 is described in SEQ ID NO:1, and its deduced amino acid sequence is described in SEQ ID NO:2. As described generally above, the zacrp2 polypeptide includes a signal sequence, ranging from amino acid 1 (Met) to amino acid residue 15 (Ala). The mature polypeptide therefore ranges from amino acid 16 (Asp) to amino acid 285 (Val). Within the mature polypeptide, an N-terminal region of no known homology is found, ranging between amino acid residue 16 (Asp) and 39 (Pro). In addition, a collagen-like domain is found between amino acid 40 (Gly) and 141 (Cys). In the collagen-like domain, 10 perfect Gly-Xaa-Pro and 24 imperfect Gly-Xaa-Xaa repeats are observed. In contrast, Acrp30 contains 22 perfect or imperfect repeats. Proline residues found in this domain at amino acid residue 45, 48, 51, 63, 84, 93, 117, 123, 135 and 138 of SEQ ID NO:2 may be hydroxylated. The zacrp2 polypeptide also includes a carboxy-terminal C1q domain, ranging from about amino acid 142 (Ser) to 285 (Val). Residue 181 (Asn) of SEQ ID NO:2 may be glycosylated. There is a fair amount of conserved structure within the C1q domain to enable proper folding. An aromatic motif (F-X(5)-[ND]-X(4)-[FYWL]-X(6)-F-X(5)-G-X-Y-X-F-X-[FY] (SEQ ID NO:5) is also found within this domain between residues 169 and 199 of SEQ ID NO:2. X represents any amino acid residue and the number in parentheses ( ) indicates the amino acid number of residues. The amino acid residues contained within the square parentheses [] restrict the choice of amino acid residues at that particular position. Zacrp2 polypeptide, human C1q C and Acrp30 appear to be homologous within the collagen domain and in the C1q domain, but not in the N-terminal portion of the mature polypeptide.

Another aspect of the present invention includes zacrp2 polypeptide fragments. Preferred fragments include those containing the collagen-like domain of zacrp2 polypeptides, ranging from amino acid 1 (Met), 16 (Asp) or 40 (Gly) to amino acid 141 (Cys) of SEQ ID NO:2, a portion of the zacrp2 polypeptide containing the collagen-like domain or a portion of the collagen-like domain capable of dimerization or oligomerization. As used herein the term "collagen" or "collagen-like domain" refers to a series of repeating triplet amino acid sequences, "repeats" or "collagen repeats" represented by the motifs Gly-Xaa-Pro or Gly-Xaa-Xaa, where Xaa is any amino acid reside. Such domains may contain as many as 34 collagen repeats or more. Fragments or proteins containing such collagen-like domains may form homomeric constructs (dimers or oligomers of the same fragment or protein). Moreover, such fragments or proteins containing such collagen-like domains may form heteromeric constructs (dimers, trimers or oligomers of different fragments or proteins).

These fragments are particularly useful in the study of collagen dimerization or oligomerization or in formation of fusion proteins as described more fully below. Polynucleotides encoding such fragments are also encompassed by the present invention, including the group consisting of (a) polynucleotide molecule comprising a sequence of nucleotides as shown in SEQ ID NO:1 from nucleotide 1, 133, 178 or 250 to nucleotide 555; (b) polynucleotide molecules that encode a zacrp2 polypeptide fragment that is at least 75% identical to the amino acid sequence of SEQ ID NO:2 from amino acid residue 40 (Gly) to amino acid residue 141 (Cys); (c) molecules complementary to (a) or (b); and (d) degenerate nucleotide sequences encoding a zacrp2 polypeptide collagen-like domain fragment.

Other preferred fragments include the globular C1q domain of zacrp2 polypeptides, ranging from amino acid 142 (Ser) to 285 (Val) of SEQ ID NO:2, a portion of the zacrp2 polypeptide containing the C1q domain or an active portion of the C1q domain. Other C1q domain containing proteins include C1q A, B and C (Sellar et al., ibid., Reid, ibid., and Reid et al., Biochem. J. 203: 559–69, 1982), chipmunk hibernation-associated plasma proteins HP-20, HP-25 and HP-27 (Takamatsu et al., Mol. Cell. Biol. 13: 1516–21, 1993 and Kondo & Kondo, J. Biol. Chem. 267: 473–8, 1992), human precerebellin (Urade et al., Proc. Natl. Acad. Sci. USA 88:1069–73, 1991), human endothelial cell multimerin (Hayward et al., J. Biol. Chem. 270:18246–51, 1995) and vertebrate collagens type VIII and X (Muragaki et al., Eur. J. Biochem. 197:615–22, 1991). The globular C1q domain of ACRP30 has been determined to have a 10 beta strand "jelly roll" topology (Shapiro and Scherer, Curr. Biol. 8:335–8, 1998) that shows significant homology to the TNF family and the zacrp2 sequence as represented by SEQ ID NO:2 contains all 10 beta-strands of this structure (amino acid residues 151–155, 172–174, 180–183, 187–190, 193–205, 208–214, 220–227, 229–241, 246–251 and 269–274 of SEQ ID NO:2). These strands have been designated "A", "A'", "B", "B'", "C", "D", "E", "F", "G" and "H" respectively.

Zacrp2 has two receptor binding loops, at amino acid residues 156–182 and 214–227 of SEQ ID NO:2. Those skilled in the art will recognize that these boundaries are approximate, and are based on alignments with known proteins and predictions of protein folding. Amino acid residues 193 (Gly), 195 (Tyr), 241 (Leu) and 270 (Phe) appear to be conserved across the superfamily including CD40, TNFα, ACRP30 and zacrp2.

These fragments are particularly useful in the study or modulation of energy balance or neurotransmission, particularly diet- or stress-related neurotransmission. Antimicrobial activity may also be present in such fragments. The homology to TNF proteins suggests such fragments would be useful in obesity-related insulin resistance, immune regulation, inflammatory response, apoptosis and osteoclast maturation. Polynucleotides encoding such fragments are also encompassed by the present invention, including the group consisting of (a) polynucleotide molecules comprising a sequence of nucleotides as shown in SEQ ID NO:1 from nucleotide 556 to nucleotide 987; (b) polynucleotide molecules that encode a zacrp2 polypeptide fragment that is at least 80% identical to the amino acid sequence of SEQ ID NO:2 from amino acid residue 142 (Ser) to amino acid residue 285 (Val); (c) molecules complementary to (a) or (b); and (d) degenerate nucleotide sequences encoding a zacrp2 polypeptide C1q domain fragment.

Other zacrp2 polypeptide fragments of the present invention include both the collagen-like domain and the C1q domain ranging from amino acid residue 40 (Gly) to 285 (Val) of SEQ ID NO:2. Polynucleotides encoding such fragments are also encompassed by the present invention, including the group consisting of (a) polynucleotide molecules comprising a sequence of nucleotides as shown in SEQ ID NO:1 from nucleotide 250 to nucleotide 987; (b) polynucleotide molecules that encode a zacrp2 polypeptide fragment that is at least 80% identical to the amino acid sequence of SEQ ID NO:2 from amino acid residue 40 (Gly) to amino acid residue 285 (Val); (c) molecules complementary to (a) or (b); and (d) degenerate nucleotide sequences encoding a zacrp2 polypeptide collagen-like domain-C1q domain fragment.

The highly conserved amino acids, particularly those in the carboxy-terminal C1q domain of the zacrp2 polypeptide, can be used as a tool to identify new family members. For instance, reverse transcription-polymerase chain reaction (RT-PCR) can be used to amplify sequences encoding the conserved motifs from RNA obtained from a variety of tissue sources. In particular, highly degenerate primers designed from conserved sequences are useful for this purpose. In particular, the following primers and their complements are useful for this purpose:

Amino acid residues 244–260 of SEQ ID NO:2 GGN GAN SAR GTN TGG YT (SEQ ID NO:6)
Amino acid residues 192–197 of SEQ ID NO:2 SN GNN NTN TAY TWY TTY R (SEQ ID NO:7)
Amino acid residues 270–275 of SEQ ID NO:2 TTY DSN GGN TTY YTN HT (SEQ ID NO:8)
Amino acid residues 179–185 of SEQ ID NO:2 Y TWY RAY RBN WBN WSN GG (SEQ ID NO:9)

Probes corresponding to complements of the polynucleotides set forth above are also encompassed.

The present invention also provides polynucleotide molecules, including DNA and RNA molecules, that encode the zacrp2 polypeptides disclosed herein. Those skilled in the art will readily recognize that, in view of the degeneracy of the genetic code, considerable sequence variation is possible among these polynucleotide molecules. SEQ ID NO:10 is a degenerate DNA sequence that encompasses all DNAs that encode the zacrp2 polypeptide of SEQ ID NO:2. Those skilled in the art will recognize that the degenerate sequence of SEQ ID NO:10 also provides all RNA sequences encoding SEQ ID NO:2 by substituting U for T. Thus, zacrp2 polypeptide-encoding polynucleotides comprising nucleotide 1 to nucleotide 855 of SEQ ID NO:10 and their RNA equivalents are contemplated by the present invention. Table 1 sets forth the one-letter codes used within SEQ ID NO:10 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
| --- | --- | --- | --- |
| A | A | T | T |
| C | C | G | G |
| G | G | C | C |
| T | T | A | A |
| R | A \| G | Y | C \| T |
| Y | C \| T | R | A \| G |

TABLE 1-continued

| Nucleotide | Resolution | Complement | Resolution |
|---|---|---|---|
| M | A \| C | K | G \| T |
| K | G \| T | M | A \| C |
| S | C \| G | S | C \| G |
| W | A \| T | W | A \| T |
| H | A \| C \| T | D | A \| G \| T |
| B | C \| G \| T | V | A \| C \| G |
| V | A \| C \| G | B | C \| G \| T |
| D | A \| G \| T | H | A \| C \| T |
| N | A \| C \| G \| T | N | A \| C \| G \| T |

The degenerate codons used in SEQ ID NO:10, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene* 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:10 serves as a template for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are zacrp2 polypeptides from other mammalian species, including murine, porcine, ovine, bovine, canine, feline, equine, and other primate polypeptides. A partial murine zacrp2 homolog (SEQ ID NO:12) has been identified. The polynucleotide sequence encoding this murine zacrp2 polypeptide disclosed in SEQ ID NO:11. Orthologs of human zacrp2 can be cloned using information and compositions provided by the present invention in combination with conventional cloning techniques. For example, a cDNA can be cloned using mRNA obtained from a tissue or cell type that expresses zacrp2 as disclosed herein. Suitable sources of mRNA can be identified by probing northern blots with probes designed from the sequences disclosed herein. A library is then prepared from mRNA of a positive tissue or cell line.

An zacrp2-encoding cDNA can then be isolated by a variety of methods, such as by probing with a complete or partial human cDNA or with one or more sets of degenerate probes based on the disclosed sequences. A cDNA can also be cloned using the polymerase chain reaction with primers designed from the representative human zacrp2 sequences disclosed herein. Within an additional method, the cDNA library can be used to transform or transfect host cells, and expression of the cDNA of interest can be detected with an antibody to zacrp2 polypeptide. Similar techniques can also be applied to the isolation of genomic clones.

Those skilled in the art will recognize that the sequence disclosed in SEQ ID NO:1 represents a single allele of human zacrp2, and that allelic variation and alternative splicing are expected to occur. Allelic variants of this sequence can be cloned by probing cDNA or genomic libraries from different individuals according to standard procedures. Allelic variants of the nucleotide sequence shown in SEQ ID NO:1, including those containing silent mutations and those in which mutations result in amino acid sequence changes, are within the scope of the present invention, as are proteins which are allelic variants of SEQ ID NO:2. cDNA molecules generated from alternatively spliced mRNAs, which retain the properties of the zacrp2 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Within preferred embodiments of the invention, the isolated nucleic acid molecules can hybridize under stringent conditions to nucleic acid molecules having the nucleotide sequence of SEQ ID NO:1 or to nucleic acid molecules having a nucleotide sequence complementary to SEQ ID NO:1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5–25° C. below the $T_m$ of the hybrid and a hybridization buffer having up to 1 M $Na^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20–70° C. and a hybridization buffer containing up to 6×SSC and 0–50% formamide. A higher degree of stringency can be achieved at temperatures of from 40–70° C. with a hybridization buffer having up to 4×SSC and from 0–50% formamide. Highly stringent conditions typically encompass temperatures of 42–70° C. with a hybridization buffer having up to 1×SSC and 0–50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual,* Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques,* (Academic Press, Inc. 1987); and Wetmur, *Crit. Rev. Biochem. Mol. Biol.* 26:227 (1990)). Sequence analysis software, such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20–25° C. below the calculated $T_m$. For smaller probes, <50 base pairs, hybridization is typically carried out at the $T_m$ or 5–10° C. below. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a $Na^+$ source, such as SSC (1×SSC: 0.15 M sodium chloride, 15 mM sodium citrate) or SSPE (1×SSPE: 1.8 M NaCl, 10 mM $NaH_2PO_4$, 1 mM EDTA, pH 7.7). By decreasing the ionic concentration of the buffer, the stability of the hybrid is increased. Typically, hybridization buffers contain from between 10 mM–1 M Na⁺. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant zacrp2 polypeptide can be hybridized with a nucleic acid molecule having the nucleotide sequence of SEQ ID NO:1 (or its complement) at 42° C. overnight in a solution comprising 50% formamide, 5×SSC (1×SSC: 0.15 M sodium chloride and 15 mM sodium citrate), 50 mM sodium phosphate (pH 7.6), 5× Denhardt's solution (100× Denhardt's solution: 2% (w/v) Ficoll 400, 2% (w/v) polyvinylpyrrolidone, and 2% (w/v) bovine serum albumin), 10% dextran sulfate, and 20 μg/ml denatured, sheared salmon sperm DNA. One of skill in the art can devise variations of these hybridization conditions. For example, the hybridization mixture can be incubated at a higher or lower temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 50–65° C. That is, nucleic acid molecules encoding a variant zacrp2 polypeptide hybridize with a nucleic acid molecule having the nucleotide sequence of SEQ ID NO:1 (or its complement) under stringent washing conditions, in which the wash stringency is equivalent to 0.5×–2×SSC with 0.1% SDS at 50–65° C., including 0.5× SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×–0.2×SSC with 0.1% sodium dodecyl sulfate (SDS) at 50–65° C. In other words, nucleic acid molecules encoding a variant zacrp2 polypeptide hybridize with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50–65° C., including 0.1×SSC with 0.1% SDS at 50° C., or 0.2×SSC with 0.1% SDS at 65° C.

The present invention also provides isolated zacrp2 polypeptides that have a substantially similar sequence identity to the polypeptides of SEQ ID NO:2, or their orthologs. The term "substantially similar sequence identity" is used herein to denote polypeptides having at least 70%, at least 80%, at least 90%, at least 95% or greater than 95% sequence identity to the sequences shown in SEQ ID NO:2, or their orthologs. The present invention also includes polypeptides that comprise an amino acid sequence having at least 70%, at least 80%, at least 90%, at least 95% or greater than 95% sequence identity to the sequence of amino acid residues 40 to 285 of SEQ ID NO:2. The present invention further includes nucleic acid molecules that encode such polypeptides. Methods for determining percent identity are described below.

The present invention also contemplates zacrp2 variant nucleic acid molecules that can be identified using two criteria: a determination of the similarity between the encoded polypeptide with the amino acid sequence of SEQ ID NO:2, and a hybridization assay, as described above. Such zacrp2 variants include nucleic acid molecules (1) that hybridize with a nucleic acid molecule having the nucleotide sequence of SEQ ID NO:1 (or its complement) under stringent washing conditions, in which the wash stringency is equivalent to 0.5×–2×SSC with 0.1% SDS at 55–65° C., and (2) that encode a polypeptide having at least 70%, at least 80%, at least 90%, at least 95% or greater than 95% sequence identity to the amino acid sequence of SEQ ID NO:2. Alternatively, zacrp2 variants can be characterized as nucleic acid molecules (1) that hybridize with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50–65° C., and (2) that encode a polypeptide having at least 70%, at least 80%, at least 90%, at least 95% or greater than 95% sequence identity to the amino acid sequence of SEQ ID NO:2.

Percent sequence identity is determined by conventional methods. See, for example, Altschul et al., *Bull. Math. Bio.* 48:603, 1986, and Henikoff and Henikoff, *Proc. Natl. Acad. Sci. USA* 89:10915, 1992. Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |

TABLE 3-continued

|   | A  | R  | N  | D  | C  | Q  | E  | G  | H  | I  | L  | K  | M  | F  | P  | S  | T  | W  | Y  | V |
|---|----|----|----|----|----|----|----|----|----|----|----|----|----|----|----|----|----|----|----|---|
| K | -1 | 2  | 0  | -1 | -3 | 1  | 1  | -2 | -1 | -3 | -2 | 5  |    |    |    |    |    |    |    |   |
| M | -1 | -1 | -2 | -3 | -1 | 0  | -2 | -3 | -2 | 1  | 2  | -1 | 5  |    |    |    |    |    |    |   |
| F | -2 | -3 | -3 | -3 | -2 | -3 | -3 | -3 | -1 | 0  | 0  | -3 | 0  | 6  |    |    |    |    |    |   |
| P | -1 | -2 | -2 | -1 | -3 | -1 | -1 | -2 | -2 | -3 | -3 | -1 | -2 | -4 | 7  |    |    |    |    |   |
| S | 1  | -1 | 1  | 0  | -1 | 0  | 0  | 0  | -1 | -2 | -2 | 0  | -1 | -2 | -1 | 4  |    |    |    |   |
| T | 0  | -1 | 0  | -1 | -1 | -1 | -1 | -2 | -2 | -1 | -1 | -1 | -1 | -2 | -1 | 1  | 5  |    |    |   |
| W | -3 | -3 | -4 | -4 | -2 | -2 | -3 | -2 | -2 | -3 | -2 | -3 | -1 | 1  | -4 | -3 | -2 | 11 |    |   |
| Y | -2 | -2 | -2 | -3 | -2 | -1 | -2 | -3 | 2  | -1 | -1 | -2 | -1 | 3  | -3 | -2 | -2 | 2  | 7  |   |
| V | 0  | -3 | -3 | -3 | -1 | -2 | -2 | -3 | -3 | 3  | 1  | -2 | 1  | -1 | -2 | -2 | 0  | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zacrp2. The FASTA algorithm is described by Pearson and Lipman, *Proc. Nat. Acad. Sci. USA* 85:2444, 1988, and by Pearson, *Meth. Enzymol.* 183:63, 1990.

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then re-scored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63, 1990.

FASTA can also be used to determine the sequence identity of nucleic acid molecules using a ratio as disclosed above. For nucleotide sequence comparisons, the ktup value can range between one to six, preferably from four to six.

The present invention includes nucleic acid molecules that encode a polypeptide having one or more "conservative amino acid substitutions," compared with the amino acid sequence of SEQ ID NO:2. Conservative amino acid substitutions can be based upon the chemical properties of the amino acids. That is, variants can be obtained that contain one or more amino acid substitutions of SEQ ID NO:2, in which an alkyl amino acid is substituted for an alkyl amino acid in a zacrp2 amino acid sequence, an aromatic amino acid is substituted for an aromatic amino acid in a zacrp2 amino acid sequence, a sulfur-containing amino acid is substituted for a sulfur-containing amino acid in a zacrp2 amino acid sequence, a hydroxy-containing amino acid is substituted for a hydroxy-containing amino acid in a zacrp2 amino acid sequence, an acidic amino acid is substituted for an acidic amino acid in a zacrp2 amino acid sequence, a basic amino acid is substituted for a basic amino acid in a zacrp2 amino acid sequence, or a dibasic monocarboxylic amino acid is substituted for a dibasic monocarboxylic amino acid in a zacrp2 amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The BLOSUM62 table is an amino acid substitution matrix derived from about 2,000 local multiple alignments of protein sequence segments, representing highly conserved regions of more than 500 groups of related proteins (Henikoff and Henikoff, *Proc. Natl. Acad. Sci. USA* 89:10915, 1992). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than -1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Conservative amino acid changes in a zacrp2 gene can be introduced by substituting nucleotides for the nucleotides recited in SEQ ID NO:1. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8–10 to 8–22; and McPherson (ed.), *Directed Mutagenesis: A Practical Approach* (IRL Press 1991)). The ability of such variants to promote the energy balance modulating or other properties of the wild-type protein can be determined using a standard methods, such as the assays described herein. Alternatively, a variant zacrp2 polypeptide can be identified by the ability to specifically bind anti-zacrp2 antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxyethyl-cysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenyl-alanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722, 1991, Ellman et al., *Methods Enzymol.* 202:301, 1991, Chung et al., *Science* 259:806, 1993, and Chung et al., *Proc. Nat. Acad. Sci. USA* 90:10145, 1993.

In a second method, translation is carried out in *Xenopus* oocytes by microinjection of mutated mRNA and chemically aminoacylated suppressor tRNAs (Turcatti et al., *J. Biol. Chem.* 271:19991, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395, 1993).

A limited number of non-conservative amino acids, amino acids that are not encoded by the genetic code, non-naturally occurring amino acids, and unnatural amino acids may be substituted for zacrp2 amino acid residues.

Multiple amino acid substitutions can be made and tested using known methods of mutagenesis and screening, such as those disclosed by Reidhaar-Olson and Sauer (*Science* 241:53, 1988) or Bowie and Sauer (*Proc. Nat. Acad. Sci. USA* 86:2152, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832, 1991, Ladner et al., U.S. Pat. No. 5,223,409, Huse, international publication No. WO 92/06204, and region-directed mutagenesis (Derbyshire et al., *Gene* 46:145, 1986, and Ner et al., *DNA* 7:127, 1988).

Variants of the disclosed zacrp2 nucleotide and polypeptide sequences can also be generated through DNA shuffling as disclosed by Stemmer, *Nature* 370:389, 1994, Stemmer, *Proc. Nat. Acad. Sci. USA* 91:10747, 1994, and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-zacrp2 antibodies, can be recovered from the host cells and rapidly sequenced using modern equipment. These methods allow the rapid determination of the importance of individual amino acid residues in a polypeptide of interest, and can be applied to polypeptides of unknown structure.

Essential amino acids in the polypeptides of the present invention can be identified according to procedures known in the art, such as site-directed mutagenesis or alanine-scanning mutagenesis (Cunningham and Wells, *Science* 244:1081, 1989, Bass et al., *Proc. Nat. Acad. Sci. USA* 88:4498, 1991, Coombs and Corey, "Site-Directed Mutagenesis and Protein Engineering," in *Proteins: Analysis and Design,* Angeletti (ed.), pages 259–311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699, 1996. The identities of essential amino acids can also be inferred from analysis of homologies with zacrp2.

The location of zacrp2 receptor binding domains can be identified by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306, 1992, Smith et al., *J. Mol. Biol.* 224:899, 1992, and Wlodaver et al., *FEBS Lett.* 309:59, 1992. Moreover, zacrp2 labeled with biotin or FITC can be used for expression cloning of zacrp2 receptors.

The present invention also provides polypeptide fragments or peptides comprising an epitope-bearing portion of a zacrp2 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat. Acad. Sci. USA* 81:3998, 1983).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660, 1983). Accordingly, antigenic epitope-bearing peptides and polypeptides of the present invention are useful to raise antibodies that bind with the polypeptides described herein.

Antigenic epitope-bearing peptides and polypeptides preferably contain at least four to ten amino acids, at least ten to fifteen amino acids, or about 15 to about 30 amino acids of SEQ ID NO:2. Such epitope-bearing peptides and polypeptides can be produced by fragmenting a zacrp2 polypeptide, or by chemical peptide synthesis, as described herein. Moreover, epitopes can be selected by phage display of random peptide libraries (see, for example, Lane and Stephen, *Curr. Opin. Immunol.* 5:268, 1993, and Cortese et al., *Curr. Opin. Biotechnol.* 7:616, 1996). Standard methods for identifying epitopes and producing antibodies from small peptides that comprise an epitope are described, for example, by Mole, "Epitope Mapping," in Methods in Molecular Biology, Vol. 10, Manson (ed.), pages 105–16 (The Humana Press, Inc. 1992), Price, "Production and Characterization of Synthetic Peptide-Derived Antibodies," in *Monoclonal Antibodies:* Production, Engineering, and Clinical Application, Ritter and Ladyman (eds.), pages 60–84 (Cambridge University Press 1995), and Coligan et al. (eds.), *Current Protocols in Immunology,* pages 9.3.1–9.3.5 and pages 9.4.1–9.4.11 (John Wiley & Sons 1997).

Regardless of the particular nucleotide sequence of a variant zacrp2 gene, the gene encodes a polypeptide that is characterized by its energy balance modulating activity or other activities of the wild-type protein, or by the ability to bind specifically to an anti-zacrp2 antibody. More specifically, variant zacrp2 genes encode polypeptides which exhibit at least 50%, and preferably, greater than 70, 80, or 90%, of the activity of polypeptide encoded by the human zacrp2 gene described herein.

For any zacrp2 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise zacrp2 variants based upon the nucleotide and amino acid sequences described herein. Accordingly, the present invention includes a computer-readable medium encoded with a data structure that provides at least one of the following sequences: SEQ ID NO:1, SEQ ID NO:2, and SEQ ID NO:10. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

The present invention also provides zacrp2 fusion proteins. For example, fusion proteins of the present invention encompass (1) a polypeptide selected from the group consisting of: (a) polypeptide molecules comprising a sequence of amino acid residues as shown in SEQ ID NO:2 from amino acid residue 1 (Met), 16 (Asp) or 40 (Gly) to amino acid residue 285 (Val); (b) polypeptide molecules ranging from amino acid 40 (Gly) to amino acid 141 (Cys) of SEQ ID NO:2, a portion of the zacrp2 polypeptide containing the collagen-like domain or a portion of the collagen-like domain capable of dimerization or oligomerization; (c) polypeptide molecules ranging from amino acid 142 (Ser) to 285 (Val) of SEQ ID NO:2, a portion of the zacrp2 polypeptide containing the C1q domain or an active portion of the C1q domain; or (d) polypeptide molecules ranging from amino acid 40 (Gly) to 285 (Val), a portion of the zacrp2 polypeptide including the collagen-like domain and the C1q domain; and (2) another polypeptide. The other polypeptide may be alternative or additional C1q domain, an alternative or additional collagen-like domain, a signal peptide to facilitate secretion of the fusion protein or the like. The globular domain of complement binds IgG, thus, the globular domain of zacrp2 polypeptide, fragment or fusion may have a similar role.

Zacrp2 polypeptides, ranging from amino acid 1 (Met) to amino acid 285 (Val); the mature zacrp2 polypeptides, ranging from amino acid 16 (Asp) to amino acid 285 (Val); or the secretion leader fragments thereof, which fragments range from amino acid 1 (Met) to amino acid 15 (Ala) may be used in the study of secretion of proteins from cells. In preferred embodiments of this aspect of the present invention, the mature polypeptides are formed as fusion proteins with putative secretory signal sequences; plasmids bearing regulatory regions capable of directing the expression of the fusion protein is introduced into test cells; and secretion of mature protein is monitored. The monitoring may be done by techniques known in the art, such as HPLC and the like.

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., ibid., and Ausubel et al. ibid.

In general, a DNA sequence encoding a zacrp2 polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zacrp2 polypeptide into the secretory pathway of a host cell, a secretory signal sequence (also known as a leader sequence, signal sequence, prepro sequence or presequence) is provided in the expression vector. The secretory signal sequence may be that of the zacrp2 polypeptide, or may be derived from another secreted protein (e.g., t-PA) or synthesized de novo. The secretory signal sequence is joined to the zacrp2 polypeptide DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830). Conversely, the signal sequence portion of the zacrp2 polypeptide (amino acids 1–15 of SEQ ID NO:2) may be employed to direct the secretion of an alternative protein by analogous methods.

The secretory signal sequence contained in the polypeptides of the present invention can be used to direct other polypeptides into the secretory pathway. The present invention provides for such fusion polypeptides. A signal fusion polypeptide can be made wherein a secretory signal sequence derived from amino acid residues 1–15 of SEQ ID NO:2 is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., Cell 14:725, 1978; Corsaro and Pearson, Somatic Cell Genetics 7:603, 1981: Graham and Van der Eb, Virology 52:456, 1973), electroporation (Neumann et al., EMBO J. 1:841–5, 1982), DEAE-dextran mediated transfection (Ausubel et al., ibid.), and liposome-mediated transfection (Hawley-Nelson et al., Focus 15:73, 1993; Ciccarone et al., Focus 15:80, 1993, and viral vectors (Miller and Rosman, BioTechniques 7:980–90, 1989; Wang and Finer, Nature Med. 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., J. Gen. Virol. 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of Agrobacterium rhizogenes as a vector for expressing genes in plant cells has been reviewed by Sinkar et al., J. Biosci. (Bangalore) 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from Autographa californica nuclear polyhedrosis virus (AcNPV). See, King and Possee, The Baculovirus Expression System: A Laboratory Guide, London, Chapman & Hall; O'Reilly et al., Baculovirus Expression Vectors: A Laboratory Manual, New York, Oxford University Press., 1994; and, Richardson, C. D., Ed., Baculovirus Expression Protocols. Methods in Molecular Biology, Totowa, N.J., Humana Press, 1995. A second method of making recombinant zacrp2 baculovirus utilizes a transposon-based system described by Luckow (Luckow et al., J. Virol. 67:4566–79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zacrp2 polypeptide into a baculovirus genome maintained in E. coli as a large plasmid called a "bacmid." The pFastBac1™ transfer vector utilizes the AcNPV polyhedrin promoter to drive the expression of the gene of interest, in this case zacrp2. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins and Possee, J. Gen. Virol. 71:971–6, 1990; Bonning et al., J. Gen. Virol. 75:1551–6, 1994; and, Chazenbalk, and Rapoport, J. Biol. Chem. 270:1543–9, 1995. In such transfer vector constructs, a short or long version of the basic protein promoter can be used. Moreover, transfer vectors can be constructed which replace the native zacrp2 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zacrp2 secretory signal sequence. In addition, transfer vectors can include an in-frame fusion with DNA encoding an epitope tag at the C- or N-terminus of the expressed zacrp2 polypeptide, for example, a Glu-Glu epitope tag (Grussenmeyer et al., Proc. Natl. Acad. Sci. 82:7952–4, 1985). Using a technique known in the art, a transfer vector containing zacrp2 is transformed into E. coli, and screened for bacmids which contain an interrupted lacZ gene indicative of recombinant baculovirus. The bacmid DNA containing the recombinant baculovirus genome is isolated, using common techniques, and used to transfect Spodoptera frugiperda cells, e.g. Sf9 cells. Recombinant virus that expresses zacrp2 is subsequently produced. Recombinant viral stocks are made by methods commonly used the art.

The recombinant virus is used to infect host cells, typically a cell line derived from the fall armyworm, Spodoptera frugiperda. See, in general, Glick and Pasternak, Molecular Biotechnology: Principles and Applications of Recombinant DNA, ASM Press, Washington, D.C., 1994. Another suitable cell line is the High FiveO™ cell line (Invitrogen) derived from Trichoplusia ni (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the T. ni cells. The cells are grown up from an inoculation density of approximately $2-5\times10^5$ cells to a density of $1-2\times10^6$ cells at which time a recombinant viral stock is added at a multiplicity of infection (MOI) of 0.1 to 10, more typically near 3. Procedures used are generally described in available laboratory manuals (King and Possee, ibid.; O'Reilly et al., ibid.; Richardson, ibid.). Subsequent purification of the zacrp2 polypeptide from the supernatant can be achieved using methods described herein.

Fungal cells, including yeast cells, can also be used within the present invention. Yeast species of particular interest in this regard include Saccharomyces cerevisiae, Pichia pastoris, and Pichia methanolica. Methods for transforming S. cerevisiae cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in Saccharomyces cerevisiae is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including Hansenula polymorpha, Schizosaccharomyces pombe, Kluyveromyces lactis, Kluyveromyces fragilis, Ustilago maydis, Pichia pastoris, Pichia methanolica, Pichia guillermondii and Candida maltosa are known in the art. See, for example, Gleeson et al., J. Gen. Microbiol. 132:3459–65, 1986 and Cregg, U.S. Pat. No. 4,882,279. Aspergillus cells may be utilized according to the methods of McKnight et al., U.S. Pat. No. 4,935,349. Methods for transforming Acremonium chrysogenum are disclosed by Sumino et al., U.S. Pat. No. 5,162,228. Methods for transforming Neurospora are disclosed by Lambowitz, U.S. Pat. No. 4,486,533.

The use of Pichia methanolica as host for the production of recombinant proteins is disclosed in WIPO Publications WO 97/17450, WO 97/17451, WO 98/02536, and WO 98/02565. DNA molecules for use in transforming P. methanolica will commonly be prepared as double-stranded, circular plasmids, which are preferably linearized prior to transformation. For polypeptide production in P. methanolica, it is preferred that the promoter and terminator in the plasmid be that of a P. methanolica gene, such as a P. methanolica alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in Pichia methanolica is a P. methanolica ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into P. methanolica cells. It is preferred to transform P. methanolica cells by electroporation using an exponentially decaying, pulsed electric field having a field strength of from 2.5 to 4.5 kV/cm, preferably about 3.75 kV/cm, and a time constant (T) of from 1 to 40 milliseconds, most preferably about 20 milliseconds.

Prokaryotic host cells, including strains of the bacteria Escherichia coli, Bacillus and other genera are also useful host cells within the present invention. Techniques for transforming these hosts and expressing foreign DNA sequences cloned therein are well known in the art (see, e.g., Sambrook et al., ibid.). When expressing a zacrp2 polypeptide in bacteria such as E. coli, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Expressed recombinant zacrp2 polypeptides (or chimeric zacrp2 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods,* Pharmacia LKB Biotechnology, Uppsala, Sweden, 1988.

The polypeptides of the present invention can be isolated by exploitation of their structural or binding properties. For example, immobilized metal ion adsorption (IMAC) chromatography can be used to purify histidine-rich proteins or proteins having a His tag. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.,* Vol. 182, "Guide to Protein Purification", M. Deutscher, (ed.), Acad. Press, San Diego, 1990, pp. 529–39). Within an additional preferred embodiments of the invention, a fusion of the polypeptide of interest and an affinity tag (e.g., maltose-binding protein, FLAG, Glu-Glu, an immunoglobulin domain) may be constructed to facilitate purification as is discussed in greater detail in the Example sections below.

Protein refolding (and optionally, reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Zacrp2 polypeptides or fragments thereof may also be prepared through chemical synthesis by methods well known in the art. Such zacrp2 polypeptides may be monomers or multimers; glycosylated or non-glycosylated; pegylated or non-pegylated; and may or may not include an initial methionine amino acid residue.

A ligand-binding polypeptide, such as a zacrp2-binding polypeptide, can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the ligand-binding polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore™, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

The invention also provides anti-zacrp2 antibodies. Antibodies to zacrp2 can be obtained, for example, using as an antigen the product of a zacrp2 expression vector, or zacrp2 isolated from a natural source. Particularly useful anti-zacrp2 antibodies "bind specifically" with zacrp2. Antibodies are considered to be specifically binding if the antibodies bind to a zacrp2 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660, 1949). Suitable antibodies include antibodies that bind with zacrp2 in particular domains.

Anti-zacrp2 antibodies can be produced using antigenic zacrp2 epitope-bearing peptides and polypeptides. Antigenic epitope-bearing peptides and polypeptides of the present invention contain a sequence of at least nine, preferably between 15 to about 30 amino acids contained within SEQ ID NO:2. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with zacrp2. It is desirable that the amino acid sequence of the epitope-bearing peptide is selected to provide substantial solubility in aqueous solvents (i.e., the sequence includes relatively hydrophilic residues, while hydrophobic residues are preferably avoided). Hydrophilic peptides can be predicted by one of skill in the art from a hydrophobicity plot, see for example, Hopp and Woods (*Proc. Nat. Acad. Sci. USA* 78:3824–8, 1981) and Kyte and Doolittle (*J. Mol. Biol.* 157: 105–142, 1982). Moreover, amino acid sequences containing proline residues may be also be desirable for antibody production.

Polyclonal antibodies to recombinant zacrp2 protein or to zacrp2 isolated from natural sources can be prepared using methods well-known to those of skill in the art. See, for example, Green et al., "Production of Polyclonal Antisera," in *Immunochemical Protocols* (Manson, ed.), pages 1–5 (Humana Press 1992), and Williams et al., "Expression of foreign proteins in *E. coli* using plasmid vectors and purification of specific polyclonal antibodies," in *DNA Cloning 2: Expression Systems,* 2nd Edition, Glover et al. (eds.), page 15 (Oxford University Press 1995). The immunogenicity of a zacrp2 polypeptide can be increased through the use of an adjuvant, such as alum (aluminum hydroxide) or Freund's complete or incomplete adjuvant. Polypeptides useful for immunization also include fusion polypeptides, such as fusions of zacrp2 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, hamsters, guinea pigs, goats, or sheep, an anti-zacrp2 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310, 1990. Antibodies can also be raised in transgenic animals such as transgenic sheep, cows, goats or pigs, and can also be expressed in yeast and fungi in modified forms as will as in mammalian and insect cells.

Alternatively, monoclonal anti-zacrp2 antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology,* Vol. 1, pages 2.5.1–2.6.7 (John Wiley & Sons 1991), Picksley et al., "Production of monoclonal antibodies against proteins expressed in *E. coli,*" in *DNA Cloning 2: Expression Systems, 2nd Edition,* Glover et al. (eds.), page 93 (Oxford University Press 1995)).

Briefly, monoclonal antibodies can be obtained by injecting mice with a composition comprising a zacrp2 gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-zacrp2 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13, 1994, Lonberg et al., Nature 368:856, 1994, and Taylor et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology,* Vol. 10, pages 79–104 (The Humana Press, Inc. 1992)).

For particular uses, it may be desirable to prepare fragments of anti-zacrp2 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230, 1960, Porter, *Biochem. J.* 73:119, 1959, Edelman et al., in *Methods in Enzymology* Vol. 1, page 422 (Academic Press 1967), and by Coligan, ibid.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Natl. Acad. Sci. USA* 69:2659, 1972. Alternatively, the variable chains can be linked by an intermolecular disulfide bond or cross-linked by chemicals such as gluteraldehyde (see, for example, Sandhu, *Crit. Rev. Biotech.* 12:437, 1992).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli.* The recombinant host cells synthesize a single polypeptide chain with a linker peptide bridging the two V domains. Methods for producing scFvs are described, for example, by Whitlow et al., *Methods: A Companion to Methods in Enzymology* 2:97, 1991, also see, Bird et al., *Science* 242:423, 1988, Ladner et al., U.S. Pat. No. 4,946,778, Pack et al., *Bio/Technology* 11:1271, 1993, and Sandhu, ibid.

As an illustration, a scFV can be obtained by exposing lymphocytes to zacrp2 polypeptide in vitro, and selecting antibody display libraries in phage or similar vectors (for instance, through use of immobilized or labeled zacrp2 protein or peptide). Genes encoding polypeptides having potential zacrp2 polypeptide binding domains can be obtained by screening random peptide libraries displayed on phage (phage display) or on bacteria, such as *E. coli.*

Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the zacrp2 sequences disclosed herein to identify proteins which bind to zacrp2.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991), Courtenay-Luck, "Genetic Manipulation of Monoclonal Antibodies," in *Monoclonal Antibodies: Production, Engineering and Clinical Application,* Ritter et al. (eds.), page 166 (Cambridge University Press, 1995), and Ward et al., "Genetic Manipulation and Expression of Antibodies," in *Monoclonal Antibodies: Principles and Applications,* Birch et al., (eds.), page 137 (Wiley-Liss, Inc. 1995)).

Alternatively, an anti-zacrp2 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat. Acad. Sci. USA* 86:3833, 1989. Techniques for producing humanized monoclonal antibodies are described, for example, by Jones et al., *Nature* 321:522, 1986, Carter et al., *Proc. Nat. Acad. Sci. USA* 89:4285, 1992, Sandhu, *Crit. Rev. Biotech.* 12:437, 1992, Singer et al., *J. Immun.* 150:2844, 1993, Sudhir (ed.), *Antibody Engineering Protocols* (Humana Press, Inc. 1995), Kelley, "Engineering Therapeutic Antibodies," in *Protein Engineering: Principles and Practice,* Cleland et al. (eds.), pages 399–434 (John Wiley & Sons, Inc. 1996), and by Queen et al., U.S. Pat. No. 5,693,762 (1997).

Polyclonal anti-idiotype antibodies can be prepared by immunizing animals with anti-zacrp2 antibodies or antibody fragments, using standard techniques. See, for example, Green et al., "Production of Polyclonal Antisera," in *Methods In Molecular Biology: Immunochemical Protocols,* Manson (ed.), pages 1–12 (Humana Press 1992). Also, see Coligan, ibid. at pages 2.4.1–2.4.7. Alternatively, monoclonal anti-idiotype antibodies can be prepared using anti-zacrp2 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875, 1996.

Genes encoding polypeptides having potential zacrp2 polypeptide binding domains, "binding proteins", can be obtained by screening random or directed peptide libraries displayed on phage (phage display) or on bacteria, such as *E. coli.* Nucleotide sequences encoding the polypeptides can be obtained in a number of ways, such as through random mutagenesis and random polynucleotide synthesis. Alternatively, constrained phage display libraries can also be produced. These peptide display libraries can be used to screen for peptides which interact with a known target which can be a protein or polypeptide, such as a ligand or receptor, a biological or synthetic macromolecule, or organic or inorganic substances. Techniques for creating and screening such peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Peptide display libraries can be screened using the zacrp2 sequences disclosed herein to identify proteins which bind to zacrp2. These "binding proteins" which interact with zacrp2 polypeptides can be used essentially like an antibody.

A variety of assays known to those skilled in the art can be utilized to detect antibodies and/or binding proteins which specifically bind to zacrp2 proteins or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant zacrp2 protein or polypeptide.

Antibodies and binding proteins to zacrp2 may be used for tagging cells that express zacrp2; for isolating zacrp2 by affinity purification; for diagnostic assays for determining circulating levels of zacrp2 polypeptides; for detecting or quantitating soluble zacrp2 as marker of underlying pathology or disease; in analytical methods employing FACS; for screening expression libraries; for generating anti-idiotypic antibodies; and as neutralizing antibodies or as antagonists to block zacrp2 polypeptide modulation of spermatogenesis or like activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Moreover, antibodies to zacrp2 or fragments thereof may be used in vitro to detect denatured zacrp2 or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zacrp2 polypeptides or anti-zacrp2 antibodies, or bioactive fragments or portions thereof, can be coupled to detectable or cytotoxic molecules and delivered to a mammal having cells, tissues or organs that express the anti-complementary molecule.

An additional aspect of the present invention provides methods for identifying agonists or antagonists of the zacrp2 polypeptides disclosed above, which agonists or antagonists may have valuable properties as discussed further herein. Within one embodiment, there is provided a method of identifying zacrp2 polypeptide agonists, comprising providing cells responsive thereto, culturing the cells in the presence of a test compound and comparing the cellular response with the cell cultured in the presence of the zacrp2 polypeptide, and selecting the test compounds for which the cellular response is of the same type.

Within another embodiment, there is provided a method of identifying antagonists of zacrp2 polypeptide, comprising providing cells responsive to a zacrp2 polypeptide, culturing a first portion of the cells in the presence of zacrp2 polypeptide, culturing a second portion of the cells in the presence of the zacrp2 polypeptide and a test compound, and detecting a decrease in a cellular response of the second portion of the cells as compared to the first portion of the cells. In addition to those assays disclosed herein, samples can be tested for inhibition of zacrp2 activity within a variety of assays designed to measure receptor binding or the stimulation/inhibition of zacrp2-dependent cellular responses. For example, zacrp2-responsive cell lines can be transfected with a reporter gene construct that is responsive to a zacrp2-stimulated cellular pathway. Reporter gene constructs of this type are known in the art, and will generally comprise a zacrp2-DNA response element operably linked to a gene encoding an assayable protein, such as luciferase. DNA response elements can include, but are not limited to, cyclic AMP response elements (CRE), hormone response elements (HRE), insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6, 1988 and Habener, *Molec. Endocrinol.* 4 (8):1087–94, 1990. Hormone response elements are reviewed in Beato, *Cell* 56:335–44; 1989. Candidate compounds, solutions, mixtures or extracts are tested for the ability to inhibit the activity of zacrp2 on the target cells as evidenced by a decrease in zacrp2 stimulation of reporter gene expression. Assays of this type will detect compounds that directly block zacrp2 binding to cell-surface receptors, as well as compounds that block processes in the cellular pathway subsequent to receptor-ligand binding. In the alternative, compounds or other samples can be tested for direct blocking of zacrp2 binding to receptor using zacrp2 tagged with a detectable label (e.g., $^{125}I$, biotin, horseradish peroxidase, FITC, and the like). Within assays of this type, the ability of a test sample to inhibit the binding of labeled zacrp2 to the receptor is indicative of inhibitory activity, which can be confirmed through secondary assays. Receptors used within binding assays may be cellular receptors or isolated, immobilized receptors.

Zacrp2 polypeptides, fragments, fusions, agonists or antagonists can be used to modulate energy balance in mammals or to protect endothelial cells from injury. With regard to modulating energy balance, zacrp2 polypeptides modulate cellular metabolic reactions. Such metabolic reactions include adipogenesis, gluconeogenesis, glycogenolysis, lipogenesis, glucose uptake, protein synthesis, thermogenesis, oxygen utilization and the like. The expression pattern of zacrp2 polypeptide indicates expression in endothelial cell tissues. With regard to endothelial cell protection, zacrp2 polypeptide may be used in organ preservation, for cryopreservation, for surgical pre-treatment to prevent injury due to ischemia and/or inflammation or in like procedures. Expression of zacrp2 polypeptide in the heart suggests that the protein may modulate acetylcholine and/or norepinephrine release. Zacrp2 polypeptides may also find use as neurotransmitters or as modulators of neurotransmission, as indicated by expression of the polypeptide in tissues associated with the sympathetic or parasympathetic nervous system. In this regard, zacrp2 polypeptides may find utility in modulating nutrient uptake, as demonstrated, for example, by 2-deoxy-glucose uptake in the brain or the like.

Expression in the aorta suggests that the protein may be involved in hemostasis. Platelets interact with damaged vessel walls to form a thrombus. The degree of response is graded due to the subendothelium tissue exposed and the blood flow in the injured area. In this regard, zacrp2 polypeptides may find utility in modulating hemostasis, increasing blood flow flowing vascular injury and pacifying collagenous surfaces.

Among other methods known in the art or described herein, mammalian energy balance may be evaluated by monitoring one or more of the following metabolic functions: adipogenesis, gluconeogenesis, glycogenolysis, lipogenesis, glucose uptake, protein synthesis, thermogenesis, oxygen utilization or the like. These metabolic functions are monitored by techniques (assays or animal models) known to one of ordinary skill in the art, as is more fully set forth below. For example, the glucoregulatory effects of insulin are predominantly exerted in the liver, skeletal muscle and adipose tissue. Insulin binds to its cellular receptor in these three tissues and initiates tissue-specific actions that result in, for example, the inhibition of glucose production and the stimulation of glucose utilization. In the liver, insulin stimulates glucose uptake and inhibits gluconeogenesis and glycogenolysis. In skeletal muscle and adipose tissue, insulin acts to stimulate the uptake, storage and utilization of glucose.

Art-recognized methods exist for monitoring all of the metabolic functions recited above. Thus, one of ordinary skill in the art is able to evaluate zacrp2 polypeptides, fragments, fusion proteins, antibodies, agonists and antagonists for metabolic modulating functions. Exemplary modulating techniques are set forth below.

Adipogenesis, gluconeogenesis and glycogenolysis are interrelated components of mammalian energy balance, which may be evaluated by known techniques using, for example, ob/ob mice or db/db mice. The ob/ob mice are inbred mice that are homozygous for an inactivating mutation at the ob (obese) locus. Such ob/ob mice are hyperphagic and hypometabolic, and are believed to be deficient in production of circulating OB protein. The db/db mice are inbred mice that are homozygous for an inactivating mutation at the db (diabetes) locus. The db/db mice display a phenotype similar to that of ob/ob mice, except db/db mice also display a diabetic phenotype. Such db/db mice are believed to be resistant to the effects of circulating OB protein. Also, various in vitro methods of assessing these parameters are known in the art.

Insulin-stimulated lipogenesis, for example, may be monitored by measuring the incorporation of $^{14}$C-acetate into triglyceride (Mackall et al. *J. Biol. Chem.* 251:6462–4, 1976) or triglyceride accumulation (Kletzien et al., *Mol. Pharmacol.* 41:393–8, 1992).

Glucose uptake may be evaluated, for example, in an assay for insulin-stimulated glucose transport. Non-transfected, differentiated L6 myotubes (maintained in the absence of G418) are placed in DMEM containing 1 g/l glucose, 0.5 or 1.0% BSA, 20 mM Hepes, and 2 mM glutamine. After two to five hours of culture, the medium is replaced with fresh, glucose-free DMEM containing 0.5 or 1.0% BSA, 20 mM Hepes, 1 mM pyruvate, and 2 mM glutamine. Appropriate concentrations of insulin or IGF-1, or a dilution series of the test substance, are added, and the cells are incubated for 20–30 minutes. $^{3}$H or $^{14}$C-labeled deoxyglucose is added to ≈50 lM final concentration, and the cells are incubated for approximately 10–30 minutes. The cells are then quickly rinsed with cold buffer (e.g. PBS), then lysed with a suitable lysing agent (e.g. 1% SDS or 1 N NaOH). The cell lysate is then evaluated by counting in a scintillation counter. Cell-associated radioactivity is taken as a measure of glucose transport after subtracting non-specific binding as determined by incubating cells in the presence of cytocholasin b, an inhibitor of glucose transport. Other methods include those described by, for example, Manchester et al., *Am. J. Physiol.* 266 (Endocrinol. Metab. 29):E326–E333, 1994 (insulin-stimulated glucose transport).

Protein synthesis may be evaluated, for example, by comparing precipitation of $^{35}$S-methionine-labeled proteins following incubation of the test cells with $^{35}$S-methionine and $^{35}$S-methionine and a putative modulator of protein synthesis.

Thermogenesis may be evaluated as described by B. Stanley in *The Biology of Neuropeptide Y and Related Peptides,* W. Colmers and C. Wahlestedt (eds.), Humana Press, Ottawa, 1993, pp. 457–509; C. Billington et al., *Am. J. Physiol.* 260:R321, 1991; N. Zarjevski et al., *Endocrinology* 133:1753, 1993; C. Billington et al., *Am. J. Physiol.* 266:R1765, 1994; Heller et al., *Am. J. Physiol.* 252(4 Pt 2): R661–7, 1987; and Heller et al., *Am. J. Physiol.* 245: R321–8, 1983. Also, metabolic rate, which may be measured by a variety of techniques, is an indirect measurement of thermogenesis.

Oxygen utilization may be evaluated as described by Heller et al., *Pflugers Arch* 369: 55–9, 1977. This method also involved an analysis of hypothalmic temperature and metabolic heat production. Oxygen utilization and thermoregulation have also been evaluated in humans as described by Haskell et al., *J. Appl. Physiol.* 51: 948–54, 1981.

Among other methods known in the art or described herein, mammalian endothelial cell tissue protection may be evaluated by monitoring the function of endothelial tissue. For example, the function of the heart (aorta) may be evaluated by monitoring acetylcholine release, norepinephrine release or like parameters. These parameters are monitored by techniques (assays or animal models) known to one of ordinary skill in the art, as is more fully set forth below.

Acetylcholine and norepinephrine release may be monitored by HPLC. Levy, *Electrophysiology of the Sinoatrial and Atrioventricular Nodes,* Alan R. Liss, Inc., 187–197, 1998, describe measurement of norepinephrine in coronary sinus effluent. In addition, animals may be electrically paced, with the results monitored as described by Elsner, *European Heart Journal* 16(*Supplement N*) 52–8, 1995, and Reiffel and Kuehnert, *PACE* 17(Part 1): 349–65, 1994.

Among other methods known in the art or described herein, neurotransmission functions may be evaluated by monitoring 2-deoxy-glucose uptake in the brain. This parameter is monitored by techniques (assays or animal models) known to one of ordinary skill in the art, for example, autoradiography. Useful monitoring techniques are described, for example, by Kilduff et al., *J. Neurosci.* 10 2463–75, 1990, with related techniques used to evaluate the "hibernating heart" as described in Gerber et al. *Circulation* 94: 651–8, 1996, and Fallavollita et al., *Circulation* 95: 1900–9, 1997.

In addition, zacrp2 polypeptides, fragments, fusions agonists or antagonists thereof may be therapeutically useful for anti-microbial applications. For example, complement component C1q plays a role in host defense against infectious agents, such as bacteria and viruses. C1q is known to exhibit several specialized functions. For example, C1q triggers the complement cascade via interaction with bound antibody or C-reactive protein (CRP). Also, C1q interacts directly with certain bacteria, RNA viruses, mycoplasma, uric acid crystals, the lipid A component of bacterial endotoxin and membranes of certain intracellular organelles. C1q binding to the C1q receptor is believed to promote phagocytosis. C1q also appears to enhance the antibody formation aspect of the host defense system. See, for example, Johnston, *Pediatr. Infect. Dis. J.* 12(11): 933–41, 1993. Thus, soluble C1q-like molecules may be useful as anti-microbial agents, promoting lysis or phagocytosis of infectious agents.

Zacrp2 fragments as well as zacrp2 polypeptides, fusion proteins, agonists, antagonists or antibodies may be evaluated with respect to their anti-microbial properties according to procedures known in the art. See, for example, Barsum et al., *Eur. Respir. J.* 8(5): 709–14, 1995; Sandovsky-Losica et al., *J. Med. Vet. Mycol* (*England*) 28(4): 279–87, 1990; Mehentee et al., *J. Gen. Microbiol.* (*England*) 135 (*Pt. 8*): 2181–8, 1989; Segal and Savage, *J. Med. Vet. Mycol.* 24: 477–9, 1986 and the like. If desired, the performance of zacrp2 in this regard can be compared to proteins known to be functional in this regard, such as proline-rich proteins, lysozyme, histatins, lactoperoxidase or the like. In addition, zacrp2 fragments, polypeptides, fusion proteins, agonists, antagonists or antibodies may be evaluated in combination with one or more anti-microbial agents to identify synergistic effects. One of ordinary skill in the art will recognize that the anti-microbial properties of zacrp2 polypeptides, fragments, fusion proteins, agonists, antagonists and antibodies may be similarly evaluated.

As neurotransmitters or neurotransmission modulators, zacrp2 polypeptide fragments as well as zacrp2 polypeptides, fusion proteins, agonists, antagonists or antibodies of the present invention may also modulate calcium ion concentration, muscle contraction, hormone secretion, DNA synthesis or cell growth, inositol phosphate turnover, arachidonate release, phospholipase-C activation, gastric emptying, human neutrophil activation or ADCC capability, superoxide anion production and the like. Evaluation of these properties can be conducted by known methods, such as those set forth herein.

The impact of zacrp2 polypeptide, fragment, fusion, antibody, agonist or antagonist on intracellular calcium level may be assessed by methods known in the art, such as those described by Dobrzanski et al., *Regulatory Peptides* 45: 341–52, 1993, and the like. The impact of zacrp2 polypeptide, fragment, fusion, agonist or antagonist on muscle contraction may be assessed by methods known in the art, such as those described by Smits & Lebebvre, *J. Auton. Pharmacol.* 14: 383–92, 1994, Belloli et al., *J. Vet.*

*Pharmacol. Therap.* 17: 379–83, 1994, Maggi et al., *Regulatory Peptides* 53: 259–74, 1994, and the like. The impact of zacrp2 polypeptide, fragment, fusion, agonist or antagonist on hormone secretion may be assessed by methods known in the art, such as those for prolactin release described by Henriksen et al., *J. Recep. Sig. Transd. Res.* 15(1–4): 529–41, 1995, and the like. The impact of zacrp2 polypeptide, fragment, fusion, agonist or antagonist on DNA synthesis or cell growth may be assessed by methods known in the art, such as those described by Dobrzanski et al., *Regulatory Peptides* 45: 341–52, 1993, and the like. The impact of zacrp2 polypeptide, fragment, fusion, agonist or antagonist on inositol phosphate turnover may be assessed by methods known in the art, such as those described by Dobrzanski et al., *Regulatory Peptides* 45: 341–52, 1993, and the like.

Also, the impact of zacrp2 polypeptide, fragment, fusion, agonist or antagonist on arachidonate release may be assessed by methods known in the art, such as those described by Dobrzanski et al., *Regulatory Peptides* 45: 341–52, 1993, and the like. The impact of zacrp2 polypeptide, fragment, fusion, agonist or antagonist on phospholipase-C activation may be assessed by methods known in the art, such as those described by Dobrzanski et al., *Regulatory Peptides* 45: 341–52, 1993, and the like. The impact of zacrp2 polypeptide, fragment, fusion, agonist or antagonist on gastric emptying may be assessed by methods known in the art, such as those described by Varga et al., *Eur. J. Pharmacol.* 286: 109–112, 1995, and the like. The impact of zacrp2 polypeptide, fragment, fusion, agonist or antagonist on human neutrophil activation and ADCC capability may be assessed by methods known in the art, such as those described by Wozniak et al., *Immunology* 78: 629–34, 1993, and the like. The impact of zacrp2 polypeptide, fragment, fusion, agonist or antagonist on superoxide anion production may be assessed by methods known in the art, such as those described by Wozniak et al., *Immunology* 78: 629–34, 1993, and the like.

Collagen is a potent inducer of platelet aggregation. This poses risks to patients recovering from vascular injuries. Inhibitors of collagen-induced platelet aggregation would be useful for blocking the binding of platelets to collagen-coated surfaces and reducing associated collagen-induced platelet aggregation. C1q is a component of the complement pathway and has been found to stimulate defense mechanisms as well as trigger the generation of toxic oxygen species that can cause tissue damage (Tenner, *Behring Inst. Mitt.* 93:241–53, 1993). C1q binding sites are found on platelets. C1q, independent of an immune binding partner, has been found to inhibit platelet aggregation but not platelet adhesion or shape change. The amino terminal region of C1q shares homology with collagen (Peerschke and Ghebrehiwet, *J. Immunol.* 145:2984–88, 1990). Inhibition of C1q and the complement pathway can be determined using methods disclosed herein or know in the art, such as described in Suba and Csako, *J. Immunol.* 117:304–9, 1976.

The impact of zacrp2 polypeptide, fragments, fusions, agonists or antagonists on collagen-mediated platelet adhesion, activation and aggregation may be evaluated using methods described herein or known in the art, such as the platelet aggregation assay (Chiang et al., *Thrombosis Res.* 37:605–12, 1985) and platelet adhesion assays (Peerschke and Ghebrehiwet, *J. Immunol.* 144:221–25, 1990). Assays for platelet adhesion to collagen and inhibition of collagen-induced platelet aggregation can be measured using methods described in Keller et al., *J. Biol. Chem.* 268:5450–6, 1993; Waxman and Connolly, *J. Biol. Chem.* 268:5445–9, 1993; Noeske-Jungblut et al., *J. Biol. Chem.* 269:5050–3 or 1994 Deckmyn et al., *Blood* 85:712–9, 1995.

The impact of zacrp2 polypeptide, fragments, fusions, agonists or antagonists on vasodilation of aortic rings can be measured according to the methods of Dainty et al., *J. Pharmacol.* 100:767, 1990 and Rhee et al., *Neurotox.* 16:179, 1995.

Various in vitro and in vivo models are available for assessing the effects of zacrp2 polypeptides, fragments, fusion proteins, antibodies, agonists and antagonists on ischemia and reperfusion injury. See for example, Shandelya et al., *Circulation* 88:2812–26, 1993; Weisman et al., *Science* 249:146–151, 1991; Buerke et al., *Circulation* 91:393–402, 1995; Horstick et al., *Circulation* 95:701–8, 1997 and Burke et al., *J. Phar. Exp. Therp.* 286:429–38, 1998. An ex vivo hamster platelet aggregation assay is described by Deckmyn et al., ibid. Bleeding times in hamsters and baboons can be measured following injection of zacrp2 polypeptides using the model described by Deckmyn et al., ibid. The formation of thrombus in response to administration of proteins of the present invention can be measured using the hamster femoral vein thrombosis model is provided by Deckmyn et al., ibid. Changes in platelet adhesion under flow conditions following administration of zacrp2 can be measured using the method described in Harsfalvi et al., *Blood* 85:705–11, 1995.

Complement inhibition and wound healing can be zacrp2 polypeptides, fragments, fusion proteins, antibodies, agonists or antagonists be assayed alone or in combination with other know inhibitors of collagen-induced platelet activation and aggregation, such as palldipin, moubatin or calin, for example.

Zacrp2 polypeptides, fragments, fusion proteins, antibodies, agonists or antagonists can be evaluated using methods described herein or known in the art, such as healing of dermal layers in pigs (Lynch et al., *Proc. Natl. Acad. Sci. USA* 84: 7696–700, 1987) and full-thickness skin wounds in genetically diabetic mice (Greenhalgh et al., *Am. J. Pathol.* 136: 1235–46, 1990), for example. The polypeptides of the present invention can be assayed alone or in combination with other known complement inhibitors as described above.

Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other nonpolymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

The results showed linkage of zacrp2 to the human chromosome 5 framework marker SHGC-57747 with a LOD score of 7.80 and at a distance of 20 cR_10000 from the marker. The use of surrounding markers positioned zacrp2 in the 5q34 region on the integrated LDB human chromosome 5 map. The present invention also provides reagents which will find use in diagnostic applications. For example, the zacrp2 gene, a probe comprising zacrp2 DNA or RNA, or a subsequence thereof can be used to determine if the zacrp2 gene is present on chromosome 5 or if a mutation has occurred. Detectable chromosomal aberrations at the zacrp2 gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level.

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–8, 1991).

Zacrp2 polypeptides may be used in the analysis of energy efficiency of a mammal. Zacrp2 polypeptides found in serum or tissue samples may be indicative of a mammals ability to store food, with more highly efficient mammals tending toward obesity. More specifically, the present invention contemplates methods for detecting zacrp2 polypeptide comprising:

exposing a sample possibly containing zacrp2 polypeptide to an antibody attached to a solid support, wherein said antibody binds to an epitope of a zacrp2 polypeptide;

washing said immobilized antibody-polypeptide to remove unbound contaminants;

exposing the immobilized antibody-polypeptide to a second antibody directed to a second epitope of a zacrp2 polypeptide, wherein the second antibody is associated with a detectable label; and detecting the detectable label. The concentration of zacrp2 polypeptide in the test sample appears to be indicative of the energy efficiency of a mammal. This information can aid nutritional analysis of a mammal. Potentially, this information may be useful in identifying and/or targeting energy deficient tissue.

A further aspect of the invention provides a method for studying insulin. Such methods of the present invention comprise incubating adipocytes in a culture medium comprising zacrp2 polypeptide, monoclonal antibody, agonist or antagonist thereof ± insulin and observing changes in adipocyte protein secretion or differentiation.

Anti-microbial protective agents may be directly acting or indirectly acting. Such agents operating via membrane association or pore forming mechanisms of action directly attach to the offending microbe. Anti-microbial agents can also act via an enzymatic mechanism, breaking down microbial protective substances or the cell wall/membrane thereof. Anti-microbial agents, capable of inhibiting microorganism proliferation or action or of disrupting microorganism integrity by either mechanism set forth above, are useful in methods for preventing contamination in cell culture by microbes susceptible to that anti-microbial activity. Such techniques involve culturing cells in the presence of an effective amount of said zacrp2 polypeptide or an agonist or antagonist thereof.

Also, zacrp2 polypeptides or agonists thereof may be used as cell culture reagents in in vitro studies of exogenous microorganism infection, such as bacterial, viral or fungal infection. Such moieties may also be used in in vivo animal models of infection.

The present invention also provides methods of studying mammalian cellular metabolism. Such methods of the present invention comprise incubating cells to be studied, for example, human vascular endothelial cells, ± zacrp2 polypeptide, monoclonal antibody, agonist or antagonist thereof and observing changes in adipogenesis, gluconeogenesis, glycogenolysis, lipogenesis, glucose uptake, or the like.

An additional aspect of the invention provides a method for studying dimerization or oligomerization. Such methods of the present invention comprise incubating zacrp2 polypeptides or fragments or fusion proteins thereof containing a collagen-like domain alone or in combination with other polypeptides bearing collagen-like domains and observing the associations formed between the collagen like domains. Such associations are indicated by HPLC, circular dichroism or the like.

Zacrp2 polypeptides, fragments, fusion proteins, antibodies, agonists or antagonists of the present invention can be used in methods for promoting blood flow within the vasculature of a mammal by reducing the number of platelets that adhere and are activated and the size of platelet aggregates. Used to such an end, Zacrp2 can be administered prior to, during or following an acute vascular injury in the mammal. Vascular injury may be due to vascular reconstruction, including but not limited to, angioplasty, coronary artery bypass graft, microvascular repair or anastomosis of a vascular graft. Also contemplated are vascular injuries due to trauma, stroke or aneurysm. In other preferred methods the vascular injury is due to plaque rupture, degradation of the vasculature, complications associated with diabetes and atherosclerosis. Plaque rupture in the coronary artery induces heart attack and in the cerebral artery induces stroke. Use of zacrp2 polypeptides, fragments, fusion proteins, antibodies, agonists or antagonists in such methods would also be useful for ameliorating whole system diseases of the vasculature associated with the immune system, such as disseminated intravascular coagulation (DIC) and SIDs. Additionally the complement inhibiting activity would be useful for treating non-vasculature immune diseases such as arteriolosclerosis.

A correlation has been found between the presence of C1q in localized ischemic myocardium and the accumulation of leukocytes following coronary occlusion and reperfusion. Release of cellular components following tissue damage triggers complement activation which results in toxic oxygen products that may be the primary cause of myocardial damage (Rossen et al., *Circ. Res.* 62:572–84, 1998 and Tenner, ibid.). Blocking the complement pathway was found to protect ischemic myocardium from reperfusion injury (Buerke et al., *J. Pharm. Exp. Therp.* 286:429–38, 1998). Proteins having complement inhibition and C1q binding activity would be useful for such purposes.

Collagen and C1q binding capabilities of adipocyte complement related protein homologs such as zacrp2 would be useful to pacify damaged collagenous tissues preventing platelet adhesion, activation or aggregation, and the activation of inflammatory processes which lead to the release of toxic oxygen products. By rendering the exposed tissue inert towards such processes as complement activity, thrombotic activity and immune activation, reduces the injurious effects of ischemia and reperfusion. In particular, such injuries would include trauma injury ischemia, intestinal strangulation, and injury associated with pre- and post-establishment of blood flow. Such polypeptides would be useful in the treatment of cardiopulmonary bypass ischemia and recesitation, myocardial infarction and post trauma vasospasm, such as stroke or percutanious transluminal angioplasty as well as accidental or surgical-induced vascular trauma.

Additionally such collagen- and C1q-binding polypeptides would be useful to pacify prosthetic biomaterials and surgical equipment to render the surface of the materials inert towards complement activation, thrombotic activity or immune activation. Such materials include, but are not limited to, collagen or collagen fragment-coated biomaterials, gelatin-coated biomaterials, fibrin-coated biomaterials, fibronectin-coated biomaterials, heparin-coated biomaterials, collagen and gel-coated stents, arterial grafts, synthetic heart valves, artificial organs or any prosthetic application exposed to blood that will bind zsig37 at greater than $1 \times 10^8$. Coating such materials can be done using methods known in the art, see for example, Rubens, U.S. Pat. No. 5,272,074.

Complement and C1q play a role in inflammation. The complement activation is initiated by binding of C1q to immunoglobulins (Johnston, *Pediatr. Infect. Dis. J.* 12:933–41, 1993; Ward and Ghetie, *Therap. Immunol.* 2:77–94, 1995). Inhibitors of C1q and complement would be useful as anti-inflammatory agents. Such application can be made to prevent infection. Additionally, such inhibitors can be administrated to an individual suffering from inflammation mediated by complement activation and binding of immune complexes to C1q. Inhibitors of C1q and complement would be useful in methods of mediating wound repair, enhancing progression in wound healing by overcoming impaired wound healing. Progression in wound healing would include, for example, such elements as a reduction in inflammation, fibroblasts recruitment, wound retraction and reduction in infection.

Ability of tumor cells to bind to collagen may contribute to the metastasis of tumors. Inhibitors of collagen binding are also useful for mediating the adhesive interactions and metastatic spread of tumors (Noeske-Jungbult et al., U.S. Pat. No. 5,723,312).

In addition, zacrp2 polypeptides, fragments, fusions agonists or antagonists thereof may be therapeutically useful for anti-microbial applications. For example, complement component C1q plays a role in host defense against infectious agents, such as bacteria and viruses. C1q is known to exhibit several specialized functions. For example, C1q triggers the complement cascade via interaction with bound antibody or C-reactive protein (CRP). Also, C1q interacts directly with certain bacteria, RNA viruses, mycoplasma, uric acid crystals, the lipid A component of bacterial endotoxin and membranes of certain intracellular organelles. C1q binding to the C1q receptor is believed to promote phagocytosis. C1q also appears to enhance the antibody formation aspect of the host defense system. See, for example, Johnston, *Pediatr. Infect. Dis. J.* 12(11): 933–41, 1993. Thus, soluble C1q-like molecules may be useful as anti-microbial agents, promoting lysis or phagocytosis of infectious agents.

The positively charged, extracellular, triple helix, collagenous domains of C1q and macrophage scavenger receptor were determined to play a role in ligand binding and were shown to have a broad binding specificity for polyanions (Acton et al., *J. Biol. Chem.* 268:3530–37, 1993). Lysophospholipid growth factor (lysophosphatidic acid, LPA) and other mitogenic anions localize at the site of damaged tissues and assist in wound repair. LPA exerts many biological effects including activation of platelets and up-regulation of matrix assembly. It is thought that LPA synergizes with other blood coagulation factors and mediates wound healing.

The collagenous domains of proteins such as C1q and macrophage scavenger receptor are know to bind acidic phospholipids such as LPA. The interaction of zacrp2 polypeptides, fragments, fusions, agonists or antagonists with mitogenic anions such as LPA can be determined using assays known in the art, see for example, Acton et al., ibid. Inhibition of inflammatory processes by polypeptides and antibodies of the present invention would also be useful in preventing infection at the wound site.

For pharmaceutical use, the proteins of the present invention can be formulated with pharmaceutically acceptable carriers for parenteral, oral, nasal, rectal, topical, transdermal administration or the like, according to conventional methods. In a preferred embodiment administration is made at or near the site of vascular injury. In general, pharmaceutical formulations will include a zacrp2 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton Pa., 19$^{th}$ ed., 1995. Therapeutic doses will generally be determined by the clinician according to accepted standards, taking into account the nature and severity of the condition to be treated, patient traits, etc. Determination of dose is within the level of ordinary skill in the art.

As used herein a "pharmaceutically effective amount" of a zsig37 polypeptide, fragment, fusion protein, agonist or antagonist is an amount sufficient to induce a desired biological result. The result can be alleviation of the signs, symptoms, or causes of a disease, or any other desired alteration of a biological system. For example, an effective amount of a zacrp2 polypeptide is that which provides either subjective relief of symptoms or an objectively identifiable improvement as noted by the clinician or other qualified observer. Such an effective amount of a zacrp2 polypeptide would provide, for example, inhibition of collagen-activated platelet activation and the complement pathway, including C1q, increase localized blood flow within the vasculature of a patient and/or reduction in injurious effects of ischemia and reperfusion. Effective amounts of the zacrp2 polypeptides can vary widely depending on the disease or symptom to be treated. The amount of the polypeptide to be administered and its concentration in the formulations, depends upon the vehicle selected, route of administration, the potency of the particular polypeptide, the clinical condition of the patient, the side effects and the stability of the compound in the formulation. Thus, the clinician will employ the appropriate preparation containing the appropriate concentration in the formulation, as well as the amount of formulation administered, depending upon clinical experience with the patient in question or with similar patients. Such amounts will depend, in part, on the particular condition to be treated, age, weight, and general health of the patient, and other factors evident to those skilled in the art. Typically a dose will be in the range of 0.01–100 mg/kg of subject. In applications such as balloon catheters the typical dose range would be 0.05–5 mg/kg of subject. Doses for specific compounds may be determined from in vitro or ex vivo studies in combination with studies on experimental animals. Concentrations of compounds found to be effective in vitro or ex vivo provide guidance for animal studies, wherein doses are calculated to provide similar concentrations at the site of action.

Polynucleotides encoding zacrp2 polypeptides are useful within gene therapy applications where it is desired to increase or inhibit zacrp2 activity. If a mammal has a mutated or absent zacrp2 gene, the zacrp2 gene can be introduced into the cells of the mammal. In one embodiment, a gene encoding a zacrp2 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zacrp2 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; WIPO Publication WO 95/07358; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zacrp2 gene transcription, such as to inhibit cell proliferation in vivo. Polynucleotides that are complementary to a segment of a zacrp2-encoding polynucleotide (e.g., a polynucleotide as set froth in SEQ ID NO:1) are designed to bind to zacrp2-encoding mRNA and to inhibit translation of such mRNA. Such antisense polynucleotides are used to inhibit expression of zacrp2 polypeptide-encoding genes in cell culture or in a subject.

Transgenic mice, engineered to express the zacrp2 gene, and mice that exhibit a complete absence of zacrp2 gene function, referred to as "knockout mice" (Snouwaert et al., *Science* 257:1083, 1992), may also be generated (Lowell et al., *Nature* 366:740–42, 1993). These mice may be employed to study the zacrp2 gene and the protein encoded thereby in an in vivo system.

The invention is further illustrated by the following non-limiting examples.

EXAMPLE 1

Tissue Distribution

Northerns were performed using Human Multiple Tissue Blots (MTN1, MTN2 and MTN3) from Clontech (Palo Alto, Calif.) were probed to determine the tissue distribution of human zacrp2. A 1039 bp cDNA probe corresponding to full length zacrp2 was obtained from the clone discussed above by restriction digest with Eco RI and Hind III restriction enzymes according to manufacturer's instructions. The restriction fragment was isolated by gel electrophoresis and purified using a Gel Extraction Kit (Qiagen, Chatsworth, Calif.) according to manufacturer's instructions. The probe was radioactively labeled using a Rediprime II DNA labeling kit (Amersham, Arlington Heights, Ill.) according to the manufacturer's specifications. The probe was purified using a NUCTRAP push column (Stratagene Cloning Systems, La Jolla, Calif.). EXPRESSHYB (Clontech, Palo Alto, Calif.) solution was used for prehybridization and as a hybridizing solution for the Northern blots. Hybridization took place overnight at 55° C., using $1.5 \times 10^6$ cpm/ml labeled probe. The blots were then washed in 2×SSC and 0.1% SDS at room temperature, then with 2×SSC and 0.1% SDS at 65° C., followed by a wash in 0.1×SSC and 0.1% SDS at 65° C. A single transcript of approximately 1.2 kb was seen in prostate, testis, liver, heart, stomach, thyroid, spinal cord and trachea.

A RNA Master Dot Blot (Clontech) that contained RNAs from various tissues that were normalized to 8 housekeeping genes were also probed and hybridized as described above. Expression was seen at low levels in all tissues, with higher expression in heart, aorta, uterus, thyroid and small intestine.

EXAMPLE 2

Chromosomal Assignment and Placement of Zacrp2

Zacrp2 was mapped to human chromosome 5 using the commercially available version of the "Stanford G3 Radiation Hybrid Mapping Panel" (Research Genetics, Inc., Huntsville, Ala.). The Stanford G3 RH Panel contains PCRable DNAs from each of 83 radiation hybrid clones of the whole human genome, plus two control DNAs (the RM donor and the A3 recipient). A publicly available WWW server by Stanford University, which is located on the Internet, allows chromosomal localization of markers.

For the mapping of zacrp2 with the Stanford G3 RH Panel, 20 µl reactions were set up in a 96-well microtiter plate (Stratagene, La Jolla, Calif.) and used in a RoboCycler Gradient 96 thermal cycler (Stratagene). Each of the 85 PCR reactions consisted of 2 µl 10× KlenTaq PCR reaction buffer (Clontech), 1.6 µl dNTPs mix (2.5 mM each, PERKIN-ELMER, Foster City, Calif.), 1 µl sense primer, ZC 20,810 (SEQ ID NO:13), 1 µl antisense primer, ZC 20,809 (SEQ ID NO:14), 2 µl RediLoad (Research Genetics, Inc.), 0.4 µl 50× Advantage KlenTaq Polymerase Mix (Clontech Laboratories, Inc.), 25 ng of DNA from an individual hybrid clone or control and ddH$_2$O for a total volume of 20 µl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 62° C. and 1 minute AND 15 seconds extension at 72° C., followed by a final 1 cycle extension of 7 minutes at 72° C. The reactions were separated by electrophoresis on a 2% agarose gel (Life Technologies, Gaithersburg, Md.).

The results showed linkage of zacrp2 to the human chromosome 5 framework marker SHGC-57747 with a LOD score of 7.80 and at a distance of 20 cR_10000 from the marker. The use of surrounding markers positions zacrp2 in the 5q34 region on the integrated LDB human chromosome 5 map (The Genetic Location Database, University of Southhampton).

EXAMPLE 3

Baculovirus Expression of Human zacrp2

An expression vector, pzacrp2cee, was prepared to express human zacrp2 polypeptides having a C-terminal Glu-Glu tag, in insect cells.

A. Construction of pzacrp2cee

An 887 bp fragment containing sequence encoding zacrp2 and polynucleotide sequence encoding BamHI and XbaI restriction sites on the 5' and 3' ends, respectively, was generated by PCR amplification from a plasmid containing zacrp2 cDNA using primers ZC23375 (SEQ ID NO:15) and ZC23376 (SEQ ID NO:16). The PCR reaction conditions were as follows: 1 cycle of 94° C. for 4 minutes, followed by 25 cycles of 94° C. for 45 seconds, 50° C. for 45 seconds, and 72° C. for 2 minutes; 1 cycle at 72° C. for 10 min; followed by a 4° C. soak. The fragment was visualized by gel electrophoresis (1% SeaPlaque/1% NuSieve). The band was excised, diluted to 0.5% agarose with 2 mM MgCl$_2$, melted at 65° C. and ligated into an BamHI/XbaI digested baculovirus expression donor vector, pZBV32L. The pZBV32L vector is a modification of the pFastBac1™ (Life Technologies, Grand Island, N.Y.) expression vector, where the polyhedron promoter has been removed and replaced with the late activating Basic Protein Promoter and the coding sequence for the Glu-Glu tag (SEQ ID NO:17) as well as a stop signal is inserted at the 3' end of the multiple cloning region). About 28 nanograms of the restriction digested zacrp2 insert and about 56 ng of the corresponding vector were ligated overnight at 16° C. The ligation mix was diluted 3 fold in TE (10 mM Tris-HCl, pH 7.5 and 1 mM EDTA) and 4 fmol of the diluted ligation mix was transformed into DH5α Library Efficiency competent cells (Life Technologies) according to manufacturer's direction by heat shock for 45 seconds in a 42° C. waterbath. The transformed DNA and cells were diluted in 450 µl of SOC media (2% Bacto Tryptone, 0.5% Bacto Yeast Extract, 10 ml 1M NaCl, 1.5 mM KCl, 10 mM MgCl$_2$, 10 mM MgSO$_4$ and 20 mM glucose) and plated onto LB plates containing 100 µg/ml ampicillin. Clones were analyzed by restriction digests and 1 µl of the positive clone was transformed into 20 µl DH10Bac Max Efficiency competent cells (GIBCO-BRL, Gaithersburg, Md.) according to manufacturer's instruction, by heat shock for 45 seconds in a 42° C. waterbath. The transformed cells were then diluted in 980 µl SOC media (2% Bacto Tryptone, 0.5% Bacto Yeast Extract, 10 ml 1M NaCl, 1.5 mM KCl, 10 mM MgCl$_2$, 10 mM MgSO$_4$ and 20 mM glucose) out grown in shaking incubator at 37° C. for four hours and plated onto Luria Agar plates containing 50 µg/ml kanamycin, 7 µg/ml gentamicin, 10 µg/ml tetracycline, IPTG and Bluo Gal. The plated cells were incubated for 48 hours at 37° C. A color selection was used to identify those cells having zacrp2cee encoding donor insert that had incorporated into the plasmid (referred to as a "bacmid"). Those colonies, which were white in color, were picked for analysis. Bacmid DNA was isolated from positive colonies using the QiaVac Miniprep8 system (Qiagen) according the manufacturer's directions. Clones were screened for the correct insert by amplifying DNA using primers to the transposable element in the bacmid via PCR using primers ZC447 (SEQ ID NO:18) and ZC976 (SEQ ID NO:19). The PCR reaction conditions were as follows: 35 cycles of 94° C. for 45 seconds, 50° C. for 45 seconds, and 72° C. for 5 minutes; 1 cycle at 72° C. for 10 min.; followed by 4° C. soak. The PCR product was run on a 1% agarose gel to check the insert size. Those having the correct insert were used to transfect Spodoptera frugiperda (Sf9) cells.

B. Transfection

Sf9 cells were seeded at 5×10$^6$ cells per 35 mm plate and allowed to attach for 1 hour at 27° C. Five microliters of bacmid DNA was diluted with 100 µl Sf-900 II SFM (Life Technologies). Six µl of CellFECTIN Reagent (Life Technologies) was diluted with 100 µl Sf-900 II SFM. The bacmid DNA and lipid solutions were gently mixed and incubated 30–45 minutes at room temperature. The media from one plate of cells were aspirated, the cells were washed 1× with 2 ml fresh Sf-900 II SFM media. Eight hundred microliters of Sf-900 II SFM was added to the lipid-DNA mixture. The wash media was aspirated and the DNA-lipid mix added to the cells. The cells were incubated at 27° C. for 4–5 hours. The DNA-lipid mix was aspirated and 2 ml of Sf-900 II media was added to each plate. The plates were incubated at 27° C., 90% humidity, for 96 hours after which the virus was harvested.

C. Primary Amplification

Sf9 cells were grown in 50 ml Sf-900 II SFM in a 125 ml shake flask to an approximate density of 0.41–0.52×10$^5$ cells/ml. They were then infected with 150 µl of the virus stock from above and incubated at 27° C. for 3 days after which time the virus was harvested according to standard methods known in the art.

EXAMPLE 4

Purification of Baculovirus Expressed Glu-Glu-Tagged zacrp2 Polypeptides

Unless otherwise noted, all operations were carried out at 4° C. A mixture of protease inhibitors were added to a 2 liter sample of conditioned media from C-terminal Glu-Glu (EE) tagged zacrp2 baculovirus-infected Sf9 cells to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). The sample was centrifuged at 10,000 rpm for 30 min at 4° C. in a Beckman JLA-10.5 rotor (Beckman Instruments) in a Beckman Avanti J25I centrifuge (Beckman Instruments) to remove cell debris. To the supernatant fraction was added a 50.0 ml sample of anti-EE Sepharose, prepared as described below, and the mixture was gently agitated on a Wheaton (Millville, N.J.) roller culture apparatus for 18.0 h at 4° C.

The mixture was poured into a 5.0×20.0 cm Econo-Column (Bio-Rad Laboratories) and the gel was washed with 30 column volumes of phosphate buffered saline (PBS). The unretained flow-through fraction was discarded. Once the absorbance of the effluent at 280 nM was less than 0.05, flow through the column was reduced to zero and the anti-EE Sepharose gel was washed with 2.0 column volumes of PBS containing 0.2 mg/ml of EE peptide (AnaSpec, San Jose, Calif.). The peptide used has the sequence Glu-Tyr-Met-Pro-Val-Asp (SEQ ID NO:20). After 1.0 hour at 4° C., flow was resumed and the eluted protein was collected. This fraction was referred to as the peptide elution. The anti-EE Sepharose gel was washed with 2.0 column volumes of 0.1 M glycine, pH 2.5, and the glycine wash was collected separately. The pH of the glycine-eluted fraction was adjusted to 7.0 by the addition of a small volume of 10×PBS and stored at 4° C.

The peptide elution was concentrated to 5.0 ml using a 5,000 molecular weight cutoff membrane concentrator (Millipore) according to the manufacturer's instructions. The concentrated peptide elution was separated from free peptide by chromatography on a 1.5×50 cm Sephadex G-50 (Pharmacia) column equilibrated in PBS at a flow rate of 1.0 ml/min using a BioCad Sprint HPLC (PerSeptive BioSystems). Two ml fractions were collected and the absorbance at 280 nM was monitored. The first peak of material absorbing at 280 nM and eluting near the void volume of the column was collected. This material represented purified zacrp2CEE. These bands were present in about equimolar amounts. Both bands showed cross-reactivity with anti-EE antibodies by Western blotting of the purified material. The protein concentration (0.254 mg/ml) of the purified proteins was determined by BCA analysis (Pierce) and the material was aliquoted, and stored at −80° C.

Preparation of Anti-EE Sepharose

A 100 ml bed volume of protein G-Sepharose (Pharmacia) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2 HCl (Pierce), dissolved in TEA, was added to a final concentration of 36 mg/ml of gel. The gel was rocked at room temperature for 45 min and the liquid was removed using the filter unit as described above. Nonspecific sites on the gel were then blocked by incubating for 10 minutes at room temperature with 5 volumes of 20 mM ethanolamine in 200 mM TEA. The gel was then washed with 5 volumes of PBS containing 0.02% sodium azide and stored in this solution at 4° C.

EXAMPLE 5

Adhesion Molecule Assays

Upon stimulation with inflammatory cytokines such as TNF (tumor necrosis factor), human microvascular bone marrow cells (TRBMEC) express cell surface adhesion molecules, including E-selectin (endothelial leukocyte adhesion molecule), V-CAM (vascular cell adhesion molecule), and I-CAM (intercellular adhesion molecule).

The effect of zacrp2 on expression of cell surface adhesion molecules was determined using microvascular bone marrow cells (TRBMEC) in a cell ELISA according to Ouchi et al., (Circulation 100:2473–7, 1999). Briefly, TRBMEC cells were grown in 96 well, flat bottom plates (Costar, Pleasanton, Calif.) until confluent. Both wild type control media and baculovirus-expressed zacrp2 media were 10× before testing (Centricon Centrifugal Filtration Unit 5,000K cutoff, Millipore Corp., Bedford, Mass.) according to manufacturer's instructions. To each well 90 µl of zacrp2-containing media or control media was added, and the plates were incubated at 37° C., 5% $CO_2$ overnight. The next day, half of the samples received 10 µl of TNFα (10 ng/ml, R&D Systems, Minneapolis, Minn.), the other samples were untreated, measuring basal expression. The plates were incubated at 37° C., 5% $CO_2$ for 4 hours.

Following incubation, the media was removed from the plates and 50 µl anti-human VCAM antibody (1:1000 dilution of 1 mg/ml stock, R&D Systems), 50 µl of anti-human ICAM-1 monoclonal antibody (1:1000 dilution of a 1 mg/ml stock, R&D Systems), or 50 µl of anti-human E-selectin antibodies (1:1000 dilution of a 1 mg/ml stock, R&D Systems) were then added to triplicate wells and the plates were incubated at 37° C., 5% $CO_2$ for 1 hour.

The antibody solution was removed and the plates were washed three times in warm RPMI+5% FBS. Following the last wash, 100 µl/well of an 0.05% gluteraldehyde solution (1:1000 of 50% gluteraldehyde in PBS) was added to the wells and the plates were incubated at room temperature for 10 minutes. The plates were washed three times with PBS and 50 µl/well of secondary antibody (1:1000 dilution of goat α-mouse IgG whole molecule HRP conjugate (Sigma Chemical Co., St. Louis, Mo.) was added to all wells. The plates were incubated for one hour at 37° C.

The plates were then washed five times with washing buffer (PBS+0.05% Tween 20) and 100 µl/well TMB solution (100 µl of 4 mg/ml Tetra methyl benzidine (Sigma) in DMSO, in 10 ml 60 mM Na Acetate pH 5.0 and 100 µl 1.2% $H_2O_2$) was added to each well. The plates were allowed to develop at room temperature for 15–20 minutes at which time the reaction was quenched by adding 100 µl/well 1M $H_2SO_4$. Plates were read at 450 nm with reference wavelength of 655 nm.

Zacrp2 showed no effect on ICAM-1 expression. Zacrp2 did have an effect on VCAM-1 expression. When compared to the maximal TNF response, zacrp2 treated cells showed about 50% inhibition. Zacrp2 also had an effect, although less, about 10% inhibition on E-selection expression.

VCAM-1 expression was measured following direct adenovirus infection of TRBMEC cells. Briefly, TRBMEC cells were directly infected with an adenovirus containing zacrp2 or the parental adenovirus strain. The virus was added at various multiplicities of infection (moi 500, 1,000 and 5,000). Cells were incubated at 37° C., 5% $CO_2$ for 43 hours. Following infection, the adenovirus-infected cells were challenged with TNFα (1 ng/ml) for 4 hours. VCAM expression was measured as described above. VCAM-1 expression was dose dependent, with greatest inhibition, 20%, at a multiplicity of infection of 5000.

A THP-1 monocyte adherence assay according to Ouchi et al., (ibid.) and Cybulsky and Gimbrone, (*Science* 251:788–91, 1991) showed the same results as were seen for VCAM-1 above.

---

What is claimed is:

1. An isolated polynucleotide encoding a polypeptide wherein the encoded polypeptide comprises a sequence of amino acid residues that is at least 95% identical in amino acid sequence to residues 16–285 of SEQ ID NO:2, and wherein said sequence comprises:

Gly-Xaa-Xaa or Gly-Xaa-Pro repeats forming a collagen domain, wherein Xaa is any amino acid; and a carboxyl-terminal C1q domain comprising 10 beta strands.

2. The isolated polynucleotide of claim 1, wherein the encoded polypeptide is at least 95% identical in amino acid sequence to residues 1–285 of SEQ ID NO:2.

3. The isolated polynucleotide of claim 1, wherein said collagen domain consists of 24 Gly-Xaa-Xaa repeats and 10 Gly-Xaa-Pro repeats.

4. The isolated polynucleotide of claim 1, wherein said carboxyl-terminal C1q domain comprises the sequence of SEQ ID NO:5.

5. The isolated polynucleotide of claim 1, wherein said carboxy-terminal C1q domain comprises amino acid residues 151–155, 172–174, 180–183, 187–190, 193–205, 208–214, 220–227, 229–241, 246–251 and 269–274 of SEQ ID NO:2.

6. The isolated polynucleotide of claim 1, wherein any differences between said polypeptide and SEQ ID NO:2 are due to conservative amino acid substitutions.

7. The isolated polynucleotide of claim 1, wherein said polypeptide specifically binds with an antibody that specifically binds with a polypeptide consisting of the amino acid sequence of SEQ ID NO:2.

8. The isolated polynucleotide of claim 1, wherein said collagen domain consists of amino acid residues 41–141 of SEQ ID NO:2.

9. The isolated polynucleotide of claim 1, wherein said carboxy-terminal C1q domain consists of amino acid residues 142–285 of SEQ ID NO:2.

10. The isolated polynucleotide of claim 1, wherein said polypeptide comprises residues 16–285 of SEQ ID NO:2.

11. An isolated polynucleotide comprising a sequence selected from the group consisting of:

a) nucleotide 1 to nucleotide 1161 of SEQ ID NO:1;

b) nucleotide 133 to nucleotide 987 of SEQ ID NO:1;
c) nucleotide 133 to nucleotide 990 of SEQ ID NO:1;
d) nucleotide 178 to nucleotide 987 of SEQ ID NO:1;
e) nucleotide 178 to nucleotide 990 of SEQ ID NO:1;
f) nucleotide sequences complementary to a), b), c), d), or e).

12. An isolated polynucleotide encoding a fusion protein, wherein the fusion protein comprises a first portion and a second portion joined by a peptide bond, and wherein the first portion comprises a polypeptide comprising amino acid residues 16–285 of SEQ ID NO:2, and wherein the second portion comprises another polypeptide.

13. An expression vector comprising the following operably linked elements:
a transcription promoter;
an isolated DNA segment encoding a polypeptide comprising a sequence of amino acid residues that is at least 95% identical in amino acid sequence to residues 16–285 of SEQ ID NO:2, wherein said sequence comprises:
Gly-Xaa-Xaa or Gly-Xaa-Pro repeats forming a collagen domain, wherein Xaa is any amino acid; and
a carboxyl-terminal C1q domain comprising 10 beta strands; and
a transcription terminator.

14. An expression vector of claim 13, wherein said DNA segment encodes a polypeptide that is at least 95% identical in amino acid sequence to residues 1–285 of SEQ ID NO:2.

15. The expression vector of claim 13, wherein said collagen domain consists of 24 Gly-Xaa-Xaa repeats and 10 Gly-Xaa-Pro repeats.

16. The expression vector of claim 13, wherein said carboxyl-terminal C1q domain comprises a sequence of SEQ ID NO:5.

17. The expression vector of claim 13, wherein said carboxy-terminal C1q domain comprises amino acid residues 151–155, 172–174, 180–183, 187–190, 193–205, 208–214, 220–227, 229–241, 246–251 and 269–274 of SEQ ID NO:2.

18. The expression vector of claim 13, wherein any differences between said polypeptide and SEQ ID NO:2 are due to conservative amino acid substitutions.

19. The expression vector of claim 13, wherein said polypeptide specifically binds with an antibody that specifically binds with a polypeptide consisting of the amino acid sequence of SEQ ID NO:2.

20. The expression vector of claim 13, wherein said collagen domain consists of amino acid residues 41–141 of SEQ ID NO:2.

21. The expression vector of claim 13, wherein said carboxy-terminal C1q domain consists of amino acid residues 142–285 of SEQ ID NO:2.

22. The expression vector of claim 13, wherein said DNA segment encodes a polypeptide comprising amino acid residues 16–285 of SEQ ID NO:2.

23. The expression vector of claim 13, wherein said DNA segment encodes a polypeptide covalently linked at the amino or carboxyl terminus to an affinity tag.

24. The expression vector of claim 13, wherein said DNA segment further encodes a secretory signal sequence operably linked to said polypeptide.

25. The expression vector of claim 13, wherein said secretory signal sequence comprises residues 1–15 of SEQ ID NO:2.

26. A cultured cell into which has been introduced an expression vector according to claim 13, wherein said cell expresses said polypeptide encoded by said DNA segment.

27. A method of producing a polypeptide comprising:
culturing a cell into which has been introduced an expression vector according to claim 13;
whereby said cell expresses said polypeptide encoded by said DNA segment; and
recovering said expressed polypeptide.

* * * * *

SEQUENCE LISTING

<160> NUMBER OF SEQ ID NOS: 23
<210> SEQ ID NO 1
<211> LENGTH: 1161
<212> TYPE: DNA
<213> ORGANISM: Homo sapiens
<220> FEATURE:
<221> NAME/KEY: CDS
<222> LOCATION: (133)...(987)

<400> SEQUENCE: 1

```
ggaaaactat gcctggggcc gacgctctgc ccggctgctg ccgctgagga aagccgggac      60
gcggagcccc gccgagagct tctttgctcc ggacgcccct ggacgtggcg ggcagccgcg     120
agggtaacca cc atg atc ccc tgg gtg ctc ctg gcc tgt gcc ctc ccc tgt    171
              Met Ile Pro Trp Val Leu Leu Ala Cys Ala Leu Pro Cys
                1               5                  10 gct gct gac cca ctg ctt ggc gcc ttt gct cgc agg gac ttc cgg aaa       219
Ala Ala Asp Pro Leu Leu Gly Ala Phe Ala Arg Arg Asp Phe Arg Lys
 15                  20                  25 ggc tcc cct caa ctg gtc tgc agc ctg cct ggc ccc cag ggc cca ccc       267
Gly Ser Pro Gln Leu Val Cys Ser Leu Pro Gly Pro Gln Gly Pro Pro
 30                  35                  40                  45 ggc ccc cca gga gcc cca ggg ccc tca gga atg atg gga cga atg ggc       315
Gly Pro Pro Gly Ala Pro Gly Pro Ser Gly Met Met Gly Arg Met Gly
                 50                  55                  60 ttt cct ggc aaa gac ggc caa gat gga cac gac ggc gac cgg ggg gac       363
Phe Pro Gly Lys Asp Gly Gln Asp Gly His Asp Gly Asp Arg Gly Asp
             65                  70                  75 agc gga gag gaa ggt cca cct ggc cgg aca ggt aac cgg gga aag cca       411
Ser Gly Glu Glu Gly Pro Pro Gly Arg Thr Gly Asn Arg Gly Lys Pro
         80                  85                  90 gga cca aag ggc aaa gcc ggg gcc att ggg cgg gct ggc ccc cgt ggc       459
Gly Pro Lys Gly Lys Ala Gly Ala Ile Gly Arg Ala Gly Pro Arg Gly
     95                 100                 105 ccc aag ggg gtc aac ggt acc ccc ggg aag cat ggc aca cca ggc aag       507
Pro Lys Gly Val Asn Gly Thr Pro Gly Lys His Gly Thr Pro Gly Lys
110                 115                 120                 125 aag ggg ccc aag ggc aag aaa ggg gag cca ggc ctc cca ggc ccc tgc       555
Lys Gly Pro Lys Gly Lys Lys Gly Glu Pro Gly Leu Pro Gly Pro Cys
                130                 135                 140 agc tgt ggc agt ggc cat acc aag tca gct ttc tcg gtg gca gtg acc       603
Ser Cys Gly Ser Gly His Thr Lys Ser Ala Phe Ser Val Ala Val Thr
            145                 150                 155 aag agc tac cca cgg gag cgg ctg ccc atc aag ttt gac aag att ctg       651
Lys Ser Tyr Pro Arg Glu Arg Leu Pro Ile Lys Phe Asp Lys Ile Leu
        160                 165                 170 atg aac gag ggt ggc cac tac aat gct tcc agc ggc aag ttc gtc tgc       699
Met Asn Glu Gly Gly His Tyr Asn Ala Ser Ser Gly Lys Phe Val Cys
    175                 180                 185
```

-continued

```
ggc gtg cct ggg atc tac tac ttc acc tac gac atc acg ctg gcc aac      747
Gly Val Pro Gly Ile Tyr Tyr Phe Thr Tyr Asp Ile Thr Leu Ala Asn
190                 195                 200                 205 aag cac ctg gcc atc ggc ctg gtg cac aac ggc cag tac cgc atc cgg      795
Lys His Leu Ala Ile Gly Leu Val His Asn Gly Gln Tyr Arg Ile Arg
                210                 215                 220 acc ttt gat gcc aac acc ggc aac cac gat gtg gcc tca ggc tcc acc      843
Thr Phe Asp Ala Asn Thr Gly Asn His Asp Val Ala Ser Gly Ser Thr
            225                 230                 235 atc ctg gct ctc aag cag ggt gac gaa gtt tgg ctg cag atc ttc tac      891
Ile Leu Ala Leu Lys Gln Gly Asp Glu Val Trp Leu Gln Ile Phe Tyr
        240                 245                 250 tca gag cag aac ggg ctc ttc tat gac cct tac tgg aca gac agc ctc      939
Ser Glu Gln Asn Gly Leu Phe Tyr Asp Pro Tyr Trp Thr Asp Ser Leu
    255                 260                 265 ttt acg ggc ttc cta atc tat gcc gac cag gat gac ccc aac gag gta      987
Phe Thr Gly Phe Leu Ile Tyr Ala Asp Gln Asp Asp Pro Asn Glu Val
270                 275                 280                 285 tagacatgcc acggcggtcc tccaggcagg gaacaagctt ctggacttgg gcttacagag   1047
caagacccca caactgtagg ctgggggtgg ggggtcgagt gagcggttct agcctcaggc   1107
tcacctcctc cgcctctttt tttccccttc attaaatcca aaccttttta ttca         1161
```

<210> SEQ ID NO 2
<211> LENGTH: 285
<212> TYPE: PRT
<213> ORGANISM: Homo sapiens

<400> SEQUENCE: 2

```
Met Ile Pro Trp Val Leu Leu Ala Cys Ala Leu Pro Cys Ala Ala Asp
1               5                   10                  15

Pro Leu Leu Gly Ala Phe Ala Arg Arg Asp Phe Arg Lys Gly Ser Pro
            20                  25                  30

Gln Leu Val Cys Ser Leu Pro Gly Pro Gln Gly Pro Pro Gly Pro Pro
        35                  40                  45

Gly Ala Pro Gly Pro Ser Gly Met Met Gly Arg Met Gly Phe Pro Gly
    50                  55                  60

Lys Asp Gly Gln Asp Gly His Asp Gly Asp Arg Gly Asp Ser Gly Glu
65                  70                  75                  80

Glu Gly Pro Pro Gly Arg Thr Gly Asn Arg Gly Lys Pro Gly Pro Lys
                85                  90                  95

Gly Lys Ala Gly Ala Ile Gly Arg Ala Gly Pro Arg Gly Pro Lys Gly
            100                 105                 110

Val Asn Gly Thr Pro Gly Lys His Gly Thr Pro Gly Lys Lys Gly Pro
        115                 120                 125

Lys Gly Lys Lys Gly Glu Pro Gly Leu Pro Gly Pro Cys Ser Cys Gly
    130                 135                 140

Ser Gly His Thr Lys Ser Ala Phe Ser Val Ala Val Thr Lys Ser Tyr
145                 150                 155                 160

Pro Arg Glu Arg Leu Pro Ile Lys Phe Asp Lys Ile Leu Met Asn Glu
                165                 170                 175

Gly Gly His Tyr Asn Ala Ser Ser Gly Lys Phe Val Cys Gly Val Pro
            180                 185                 190

Gly Ile Tyr Tyr Phe Thr Tyr Asp Ile Thr Leu Ala Asn Lys His Leu
        195                 200                 205

Ala Ile Gly Leu Val His Asn Gly Gln Tyr Arg Ile Arg Thr Phe Asp
```

```
            210                 215                 220
Ala Asn Thr Gly Asn His Asp Val Ala Ser Gly Ser Thr Ile Leu Ala
225                 230                 235                 240

Leu Lys Gln Gly Asp Glu Val Trp Leu Gln Ile Phe Tyr Ser Glu Gln
                245                 250                 255

Asn Gly Leu Phe Tyr Asp Pro Tyr Trp Thr Asp Ser Leu Phe Thr Gly
                260                 265                 270

Phe Leu Ile Tyr Ala Asp Gln Asp Pro Asn Glu Val
                275                 280                 285

<210> SEQ ID NO 3
<211> LENGTH: 244
<212> TYPE: PRT
<213> ORGANISM: Homo sapiens

<400> SEQUENCE: 3

Met Leu Leu Leu Gly Ala Val Leu Leu Leu Ala Leu Pro Gly His
1               5                   10                  15

Asp Gln Glu Thr Thr Gln Gly Pro Gly Val Leu Leu Pro Leu Pro
                20                  25                  30

Lys Gly Ala Cys Thr Gly Trp Met Ala Gly Ile Pro Gly His Pro Gly
                35                  40                  45

His Asn Gly Ala Pro Gly Arg Asp Gly Arg Asp Gly Thr Pro Gly Glu
            50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
                100                 105                 110

Ser Ala Phe Ser Val Gly Leu Glu Thr Tyr Val Thr Ile Pro Asn Met
            115                 120                 125

Pro Ile Arg Phe Thr Lys Ile Phe Tyr Asn Gln Gln Asn His Tyr Asp
        130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 4
<211> LENGTH: 245
<212> TYPE: PRT
<213> ORGANISM: Homo sapiens

<400> SEQUENCE: 4

Met Asp Val Gly Pro Ser Ser Leu Pro His Leu Gly Leu Lys Leu Leu
1               5                   10                  15
```

```
Leu Leu Leu Leu Leu Ala Leu Arg Gly Gln Ala Asn Thr Gly Cys
             20                  25                  30

Tyr Gly Ile Pro Gly Met Pro Gly Leu Pro Gly Ala Pro Gly Lys Asp
             35                  40                  45

Gly Tyr Asp Gly Leu Pro Gly Pro Lys Gly Glu Pro Gly Ile Pro Ala
     50                  55                  60

Ile Pro Gly Ile Arg Gly Pro Lys Gly Gln Lys Gly Glu Pro Gly Leu
65                  70                  75                  80

Pro Gly His Pro Gly Lys Asn Gly Pro Met Gly Pro Pro Gly Met Pro
                 85                  90                  95

Gly Val Pro Gly Pro Met Gly Ile Pro Gly Glu Pro Gly Glu Glu Gly
            100                 105                 110

Arg Tyr Lys Gln Lys Phe Gln Ser Val Phe Thr Val Thr Arg Gln Thr
            115                 120                 125

His Gln Pro Pro Ala Pro Asn Ser Leu Ile Arg Phe Asn Ala Val Leu
    130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Ser Gly Val Lys Val Val Thr Phe
            180                 185                 190

Cys Gly His Thr Ser Lys Thr Asn Gln Val Asn Ser Gly Gly Val Leu
            195                 200                 205

Leu Arg Leu Gln Val Gly Glu Glu Val Trp Leu Ala Val Asn Asp Tyr
    210                 215                 220

Tyr Asp Met Val Gly Ile Gln Gly Ser Asp Ser Val Phe Ser Gly Phe
225                 230                 235                 240

Leu Leu Phe Pro Asp
                245

<210> SEQ ID NO 5
<211> LENGTH: 31
<212> TYPE: PRT
<213> ORGANISM: Artificial Sequence
<220> FEATURE:
<223> OTHER INFORMATION: Aromatic motif
<220> FEATURE:
<221> NAME/KEY: VARIANT
<222> LOCATION: (2)...(6)
<223> OTHER INFORMATION: Each Xaa is independently any amino acid residue.
<220> FEATURE:
<221> NAME/KEY: VARIANT
<222> LOCATION: (7)...(7)
<223> OTHER INFORMATION: Xaa is asparagine or  aspartic acid.
<220> FEATURE:
<221> NAME/KEY: VARIANT
<222> LOCATION: (8)...(11)
<223> OTHER INFORMATION: Each Xaa is independently any amino acid residue.
<220> FEATURE:
<221> NAME/KEY: VARIANT
<222> LOCATION: (12)...(12)
<223> OTHER INFORMATION: Xaa is phenylalanine, tyrosine, tryptophan or
      leucine.
<220> FEATURE:
<221> NAME/KEY: VARIANT
<222> LOCATION: (13)...(18)
<223> OTHER INFORMATION: Each Xaa is independently any amino acid residue.
<220> FEATURE:
<221> NAME/KEY: VARIANT
<222> LOCATION: (20)...(24)
<223> OTHER INFORMATION: Each Xaa is independently any amino acid residue.
<220> FEATURE:
```

```
<221> NAME/KEY: VARIANT
<222> LOCATION: (26)...(26)
<223> OTHER INFORMATION: Xaa is any amino acid residue.
<220> FEATURE:
<221> NAME/KEY: VARIANT
<222> LOCATION: (28)...(28)
<223> OTHER INFORMATION: Xaa is any amino acid residue.
<220> FEATURE:
<221> NAME/KEY: VARIANT
<222> LOCATION: (30)...(30)
<223> OTHER INFORMATION: Xaa is any amino acid residue.
<220> FEATURE:
<221> NAME/KEY: VARIANT
<222> LOCATION: (31)...(31)
<223> OTHER INFORMATION: Xaa is phenylalanine or tyrosine.

<400> SEQUENCE: 5

Phe Xaa Xaa Xaa Xaa Xaa Xaa Xaa Xaa Xaa Xaa Xaa Xaa Xaa Xaa
 1               5                  10                  15

Xaa Xaa Phe Xaa Xaa Xaa Xaa Xaa Gly Xaa Tyr Xaa Phe Xaa Xaa
             20                  25                  30

<210> SEQ ID NO 6
<211> LENGTH: 17
<212> TYPE: DNA
<213> ORGANISM: Artificial Sequence
<220> FEATURE:
<223> OTHER INFORMATION: Degenerate nucleotide primer
<220> FEATURE:
<221> NAME/KEY: variation
<222> LOCATION: (1)...(17)
<223> OTHER INFORMATION: n = A, T, G or C

<400> SEQUENCE: 6
ggngansarg tntggyt                                                  17

<210> SEQ ID NO 7
<211> LENGTH: 18
<212> TYPE: DNA
<213> ORGANISM: Artificial Sequence
<220> FEATURE:
<223> OTHER INFORMATION: Degenerate nucleotide primer
<220> FEATURE:
<221> NAME/KEY: variation
<222> LOCATION: (1)...(18)
<223> OTHER INFORMATION: n = A, T, G or C

<400> SEQUENCE: 7
snggnntnta ytwyttyr                                                 18

<210> SEQ ID NO 8
<211> LENGTH: 17
<212> TYPE: DNA
<213> ORGANISM: Artificial Sequence
<220> FEATURE:
<223> OTHER INFORMATION: Degenerate nucleotide primer
<220> FEATURE:
<221> NAME/KEY: variation
<222> LOCATION: (1)...(17)
<223> OTHER INFORMATION: n = A, T, G or C

<400> SEQUENCE: 8
ttydsnggnt tyytnht                                                  17

<210> SEQ ID NO 9
<211> LENGTH: 18
<212> TYPE: DNA
<213> ORGANISM: Artificial Sequence
<220> FEATURE:
<223> OTHER INFORMATION: Degenerate nucleotide primer
```

-continued

```
<220> FEATURE:
<221> NAME/KEY: variation
<222> LOCATION: (1)...(18)
<223> OTHER INFORMATION: n = A, T, G or C

<400> SEQUENCE: 9
ytwyrayrbn wbnwsngg                                              18

<210> SEQ ID NO 10
<211> LENGTH: 855
<212> TYPE: DNA
<213> ORGANISM: Artificial Sequence
<220> FEATURE:
<223> OTHER INFORMATION: Degenerate nucleotide sequence encoding the
      polypeptide of SEQ ID NO:2.
<220> FEATURE:
<221> NAME/KEY: variation
<222> LOCATION: (1)...(855)
<223> OTHER INFORMATION: n = A, T, G or C

<400> SEQUENCE: 10
atgathccnt gggtnytnyt ngcntgygcn ytnccntgyg cngcngaycc nytnytnggn    60
gcnttygcnm gnmgngaytt ymgnaarggn wsnccncary tngtntgyws nytnccnggn   120
ccncarggnc cnccnggncc nccnggngcn ccnggnccnw snggnatgat gggnmgnatg   180
ggnttyccng gnaargaygg ncargaygggn caygayggng aymgnggnga ywsnggngar  240
garggnccnc cnggnmgnac nggnaaymgn ggnaarccng gnccnaargg naargcnggn  300
gcnathggnm gngcnggncc nmgnggnccn aarggngtna ayggnacncc nggnaarcay  360
ggnacnccng gnaaraargg nccnaarggn aaraarggng arccnggnyt nccnggnccn  420
tgywsntgyg gnwsnggnca yacnaarwsn gcnttywsng tngcngtnac naarwsntay  480
ccnmgngarm gnytnccnat haarttygay aarathytna tgaaygargg nggncaytay  540
aaygcnwsnw snggnaartt ygtntgyggn gtnccnggna thtaytaytt yacntaygay  600
athacnytng cnaayaarca yytngcnath ggnytngtnc ayaayggnca rtaymgnath  660
mgnacnttyg aygcnaayac nggnaaycay gaygtngcnw snggnwsnac nathytngcn  720
ytnaarcarg gngaygargt ntggytncar athttytayw sngarcaraa yggnytntty  780
taygayccnt aytggacnga ywsnytntty acnggnttyy tnathtaygc ngaycargay  840
gayccnaayg argtn                                                   855

<210> SEQ ID NO 11
<211> LENGTH: 536
<212> TYPE: DNA
<213> ORGANISM: Mus musculus
<220> FEATURE:
<221> NAME/KEY: CDS
<222> LOCATION: (1)...(360)
<220> FEATURE:
<221> NAME/KEY: variation
<222> LOCATION: (1)...(536)
<223> OTHER INFORMATION: n = A, T, G or C

<400> SEQUENCE: 11 atc aag ttt gac aag att ctg atg aac gag ggt ggc cac tac aac gcg   48
Ile Lys Phe Asp Lys Ile Leu Met Asn Glu Gly Gly His Tyr Asn Ala
 1               5                  10                  15 tcc agt ggc aag ttc gtc tgc agc gtg ccg ggg atc tna tta cnt tta   96
Ser Ser Gly Lys Phe Val Cys Ser Val Pro Gly Ile Xaa Leu Xaa Leu
                20                  25                  30 cct atg aca tta cgc ntg gcc aac aaa cac ctn gnc atc ggc ctg gtg  144
Pro Met Thr Leu Arg Xaa Ala Asn Lys His Leu Xaa Ile Gly Leu Val
```

```
                35                  40                  45
cac aat ggt cag tac cgc att cgg act ttt gat gcc aac acg ggc aac    192
His Asn Gly Gln Tyr Arg Ile Arg Thr Phe Asp Ala Asn Thr Gly Asn
     50                  55                  60 cac gac gtg gcc tcg ggc tcc acc atc cta gct ctc aag gag ggt gat    240
His Asp Val Ala Ser Gly Ser Thr Ile Leu Ala Leu Lys Glu Gly Asp
 65                  70                  75                  80 gaa gtc tgg ctg cag atc ttc tac tca gag cag aat ggc ctc ttc tac    288
Glu Val Trp Leu Gln Ile Phe Tyr Ser Glu Gln Asn Gly Leu Phe Tyr
                 85                  90                  95 gac cct tac tgg acc gac agc ctg ttc acc ggc ttc ctc atc tac gct    336
Asp Pro Tyr Trp Thr Asp Ser Leu Phe Thr Gly Phe Leu Ile Tyr Ala
            100                 105                 110 gac caa gga gac ccc aac gag gta tagacaagcc ggggttgagc cttgaggtag    390
Asp Gln Gly Asp Pro Asn Glu Val
            115                 120 ggactaagag tctgcgtggg tgcctggagg aagatccctc gactgggct gtggactgac    450 aatcttggga tcttttattc ccaggcaggc ctcctctatt gctgcttaaa aagaaatca    510 ttaaatccaa gctattgatt catcta                                       536

<210> SEQ ID NO 12
<211> LENGTH: 120
<212> TYPE: PRT
<213> ORGANISM: Mus musculus
<220> FEATURE:
<221> NAME/KEY: VARIANT
<222> LOCATION: 29
<223> OTHER INFORMATION: Xaa is any amino acid
<220> FEATURE:
<221> NAME/KEY: VARIANT
<222> LOCATION: 31
<223> OTHER INFORMATION: Xaa is any amino acid
<220> FEATURE:
<221> NAME/KEY: VARIANT
<222> LOCATION: 38
<223> OTHER INFORMATION: Xaa is any amino acid
<220> FEATURE:
<221> NAME/KEY: VARIANT
<222> LOCATION: 44
<223> OTHER INFORMATION: Xaa is any amino acid

<400> SEQUENCE: 12

Ile Lys Phe Asp Lys Ile Leu Met Asn Glu Gly Gly His Tyr Asn Ala
 1               5                  10                  15

Ser Ser Gly Lys Phe Val Cys Ser Val Pro Gly Ile Xaa Leu Xaa Leu
                20                  25                  30

Pro Met Thr Leu Arg Xaa Ala Asn Lys His Leu Xaa Ile Gly Leu Val
            35                  40                  45

His Asn Gly Gln Tyr Arg Ile Arg Thr Phe Asp Ala Asn Thr Gly Asn
     50                  55                  60

His Asp Val Ala Ser Gly Ser Thr Ile Leu Ala Leu Lys Glu Gly Asp
 65                  70                  75                  80

Glu Val Trp Leu Gln Ile Phe Tyr Ser Glu Gln Asn Gly Leu Phe Tyr
                 85                  90                  95

Asp Pro Tyr Trp Thr Asp Ser Leu Phe Thr Gly Phe Leu Ile Tyr Ala
            100                 105                 110

Asp Gln Gly Asp Pro Asn Glu Val
            115                 120

<210> SEQ ID NO 13
<211> LENGTH: 18
```

```
<212> TYPE: DNA
<213> ORGANISM: Artificial Sequence
<220> FEATURE:
<223> OTHER INFORMATION: Oligonucleotide ZC20810

<400> SEQUENCE: 13
gggcttccta atctatgc                                                  18

<210> SEQ ID NO 14
<211> LENGTH: 18
<212> TYPE: DNA
<213> ORGANISM: Artificial Sequence
<220> FEATURE:
<223> OTHER INFORMATION: Oligonucleotide ZC20809

<400> SEQUENCE: 14
tggggtcttg ctctgtaa                                                  18

<210> SEQ ID NO 15
<211> LENGTH: 25
<212> TYPE: DNA
<213> ORGANISM: Artificial Sequence
<220> FEATURE:
<223> OTHER INFORMATION: Oligonucleotide ZC23375

<400> SEQUENCE: 15
gcgagggtag gatccatgat ccccct                                         25

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide ZC23376

<400> SEQUENCE: 16
gccgtggtct agatatacct cgt                                            23

<210> SEQ ID NO 17
<211> LENGTH: 7
<212> TYPE: PRT
<213> ORGANISM: Artificial Sequence
<220> FEATURE:
<223> OTHER INFORMATION: Glu-Glu tag

<400> SEQUENCE: 17

Glu Glu Tyr Met Pro Met Glu
 1               5

<210> SEQ ID NO 18
<211> LENGTH: 17
<212> TYPE: DNA
<213> ORGANISM: Artificial Sequence
<220> FEATURE:
<223> OTHER INFORMATION: Oligonucleotide ZC447

<400> SEQUENCE: 18
taacaatttc acacagg                                                   17

<210> SEQ ID NO 19
<211> LENGTH: 18
<212> TYPE: DNA
<213> ORGANISM: Artificial Sequence
<220> FEATURE:
<223> OTHER INFORMATION: Oligonucleotide ZC976

<400> SEQUENCE: 19
```

-continued

```
cgttgtaaaa cgacggcc                                              18

<210> SEQ ID NO 20
<211> LENGTH: 6
<212> TYPE: PRT
<213> ORGANISM: Artificial Sequence
<220> FEATURE:
<223> OTHER INFORMATION: purification peptide

<400> SEQUENCE: 20

Glu Tyr Met Pro Val Asp
 1               5

<210> SEQ ID NO 21
<211> LENGTH: 12
<212> TYPE: DNA
<213> ORGANISM: Artificial Sequence
<220> FEATURE:
<223> OTHER INFORMATION: Representative contig

<400> SEQUENCE: 21
atggcttagc tt                                                    12

<210> SEQ ID NO 22
<211> LENGTH: 12
<212> TYPE: DNA
<213> ORGANISM: Artificial Sequence
<220> FEATURE:
<223> OTHER INFORMATION: Representative contig

<400> SEQUENCE: 22
tagcttgagt ct                                                    12

<210> SEQ ID NO 23
<211> LENGTH: 12
<212> TYPE: DNA
<213> ORGANISM: Artificial Sequence
<220> FEATURE:
<223> OTHER INFORMATION: Representative contig

<400> SEQUENCE: 23
agccatcagc tg                                                    12
```